United States Patent [19]
Kriesel et al.

[11] Patent Number: 6,086,561
[45] Date of Patent: Jul. 11, 2000

[54] FLUID DELIVERY APPARATUS WITH RESERVOIR FILL ASSEMBLY

[75] Inventors: Marshall S. Kriesel, Saint Paul; Jmaes M. Garrison, Minneapolis; Steven Arnold, Minnetonka; Farhad Kazemzadeh, Bloomington, all of Minn.

[73] Assignee: Science Incorporated, Bloomington, Minn.

[21] Appl. No.: 09/250,036

[22] Filed: Feb. 12, 1999

Related U.S. Application Data

[63] Continuation-in-part of application No. 09/017,047, Feb. 2, 1998, Pat. No. 5,962,794, which is a continuation-in-part of application No. 08/718,686, Sep. 24, 1996, Pat. No. 5,721, 382, which is a continuation-in-part of application No. 08/432,220, May 1, 1995, abandoned.

[51] Int. Cl.$^7$ ................................................ A61M 37/00
[52] U.S. Cl. .......................... 604/133; 604/153; 604/184
[58] Field of Search ............................... 604/85, 89, 131, 604/132, 133, 151, 153, 156, 185, 191, 890.1, 184

[56] References Cited

U.S. PATENT DOCUMENTS 5,176,641  1/1993  Idriss ........................................ 604/133

*Primary Examiner*—Wynn Wood Coggins
*Assistant Examiner*—A. T. Nguyen
*Attorney, Agent, or Firm*—James E. Brunton

[57] ABSTRACT

An apparatus for delivering fluids at a precisely controlled rate which includes a fluid dispensing component having a fluid reservoir for containing the fluids to be delivered and a reservoir fill component which can be removably interconnected with the fluid dispensing component. The reservoir fill assembly is uniquely designed to accept a vial component of conventional construction which is factory filled with the medicinal fluid to be delivered to the patient. The dispenser component embodies a highly novel fluid flow indicator that provides a readily discernible visual indication of fluid flow status through the device.

39 Claims, 16 Drawing Sheets

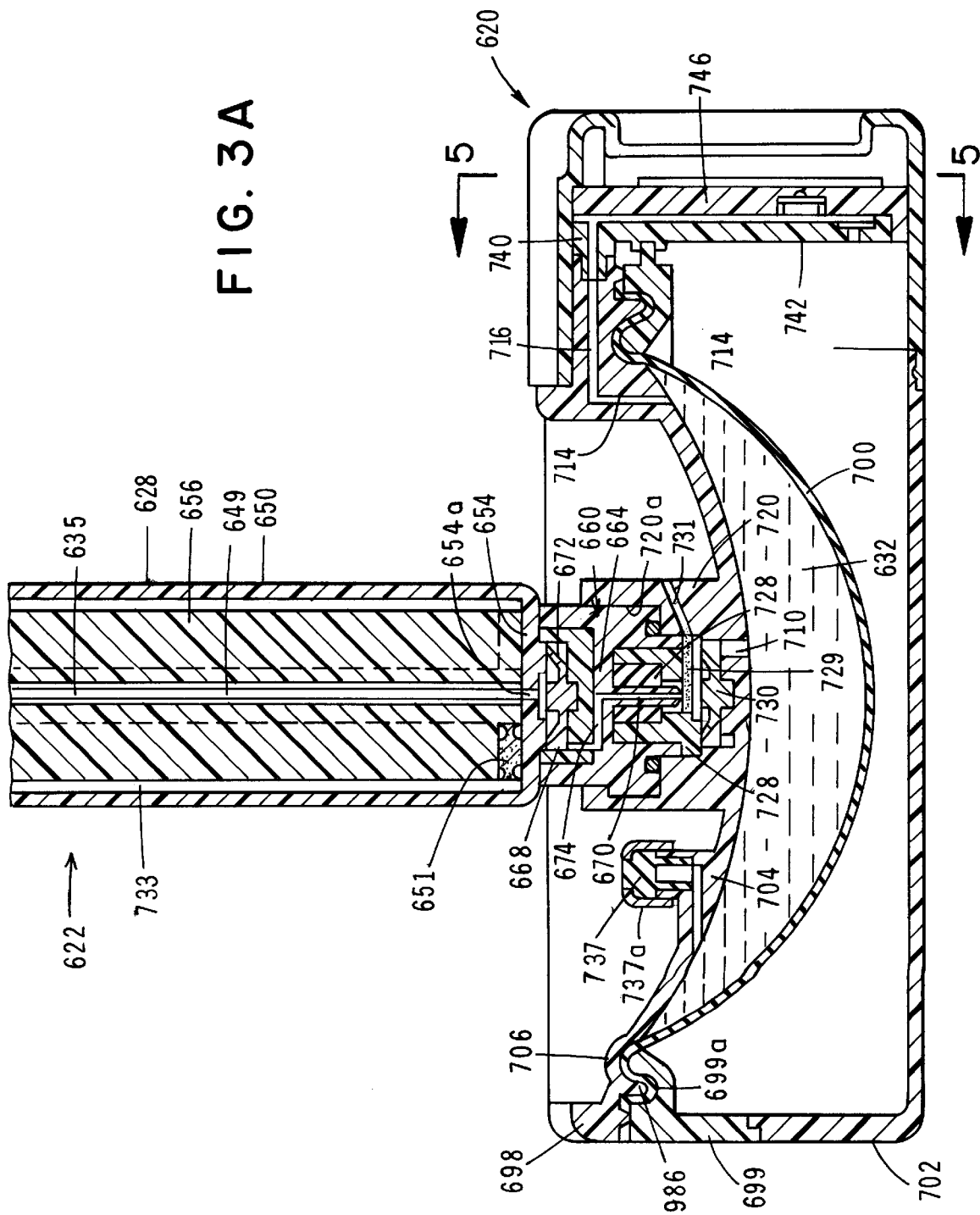

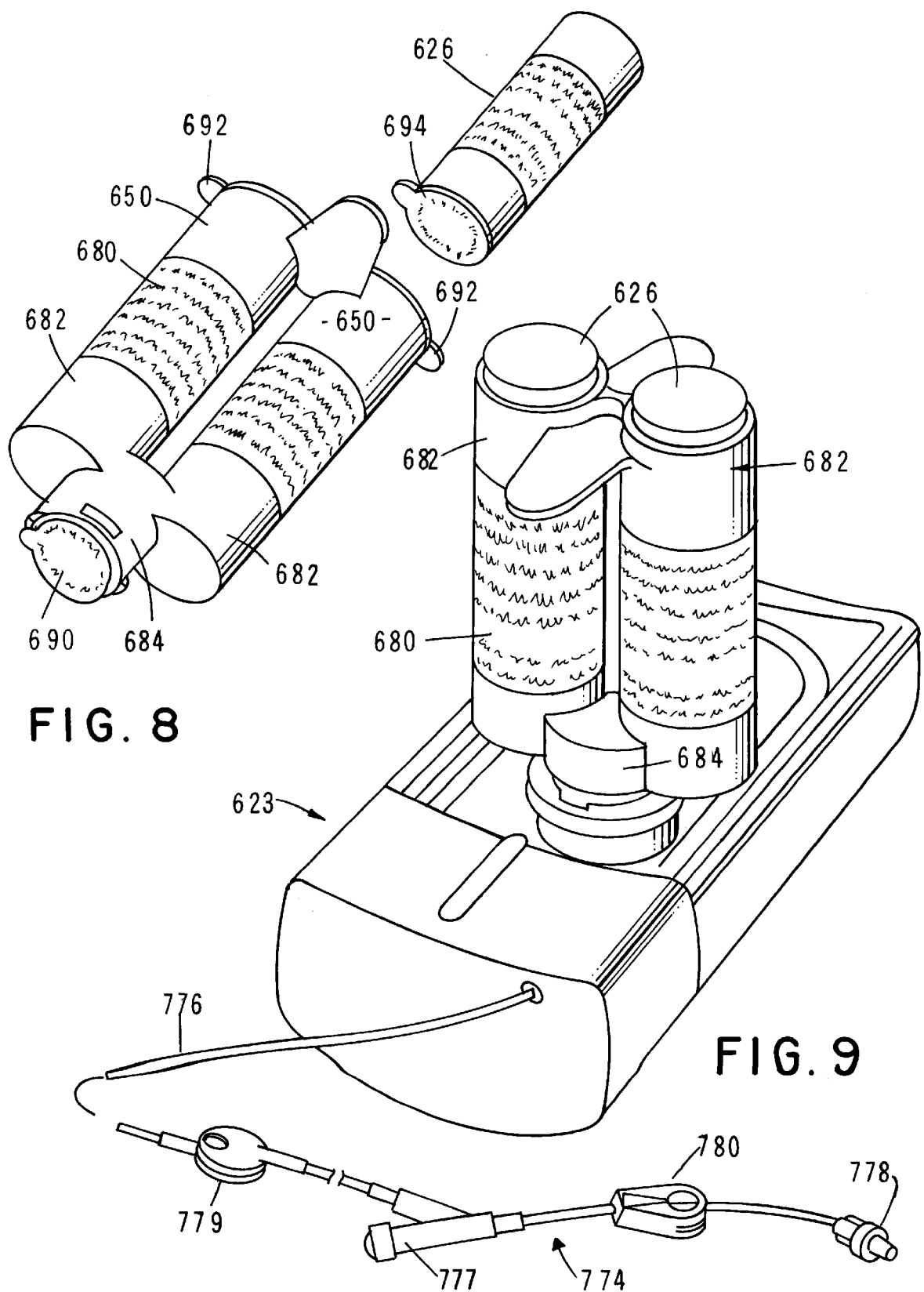

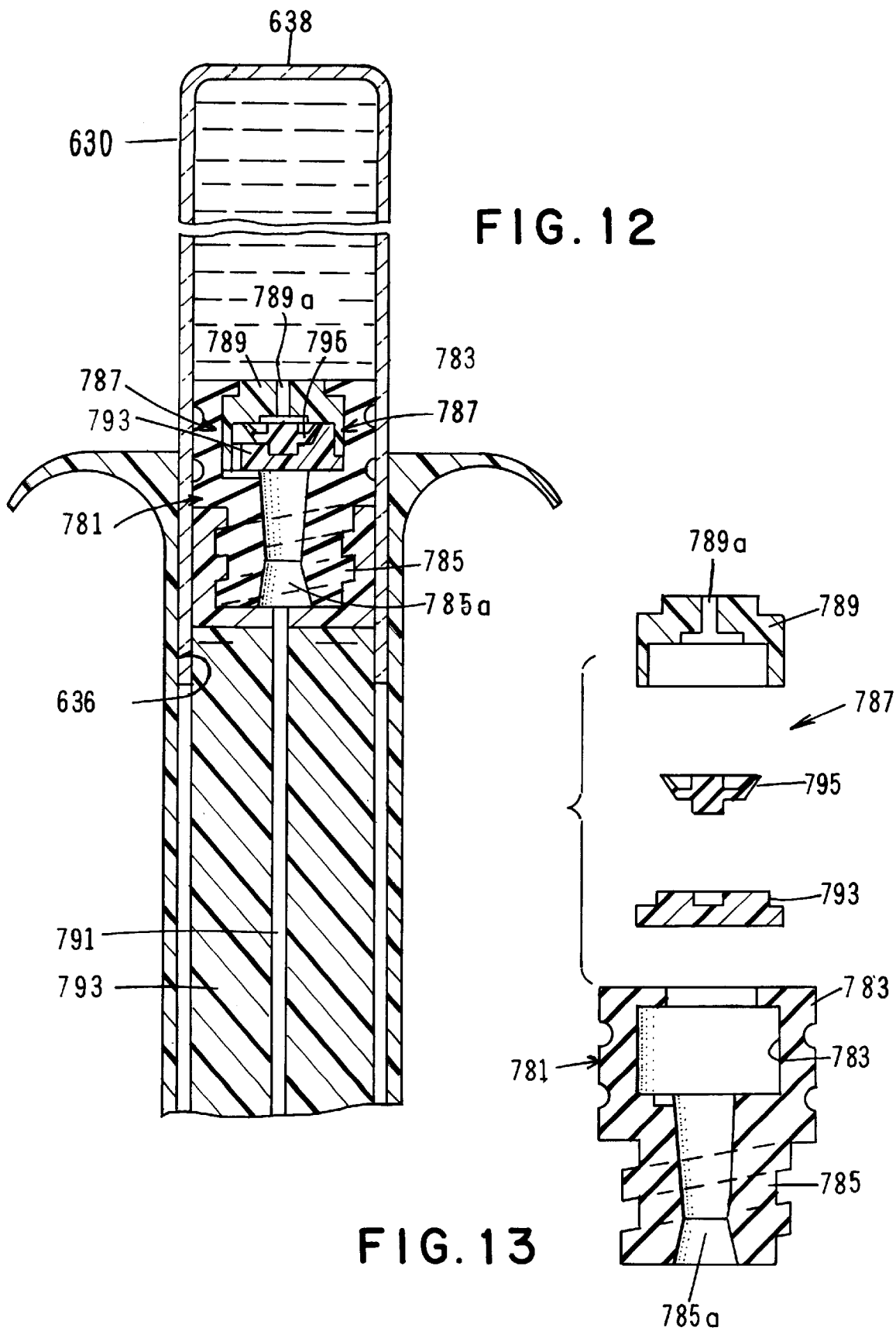

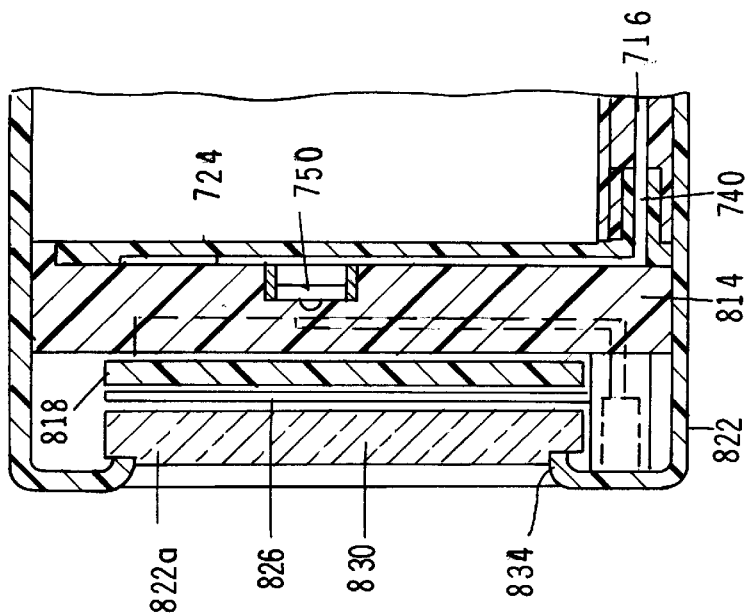
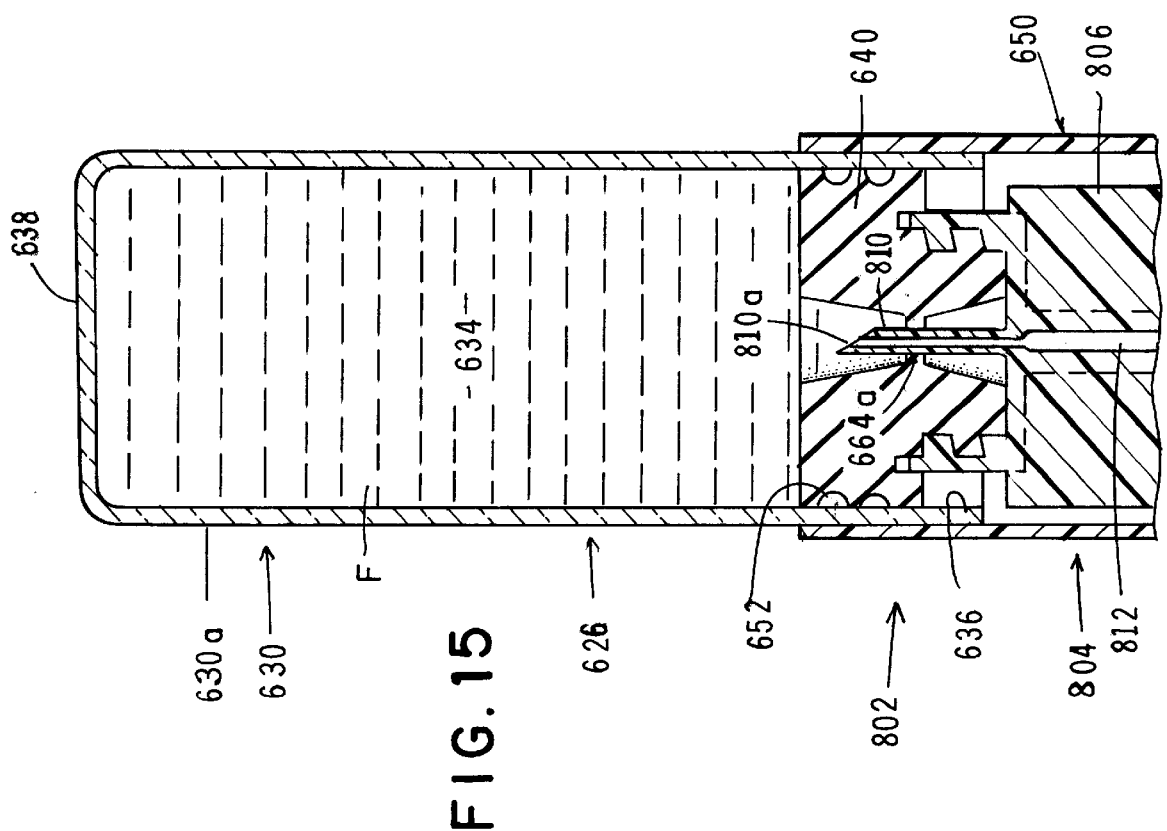

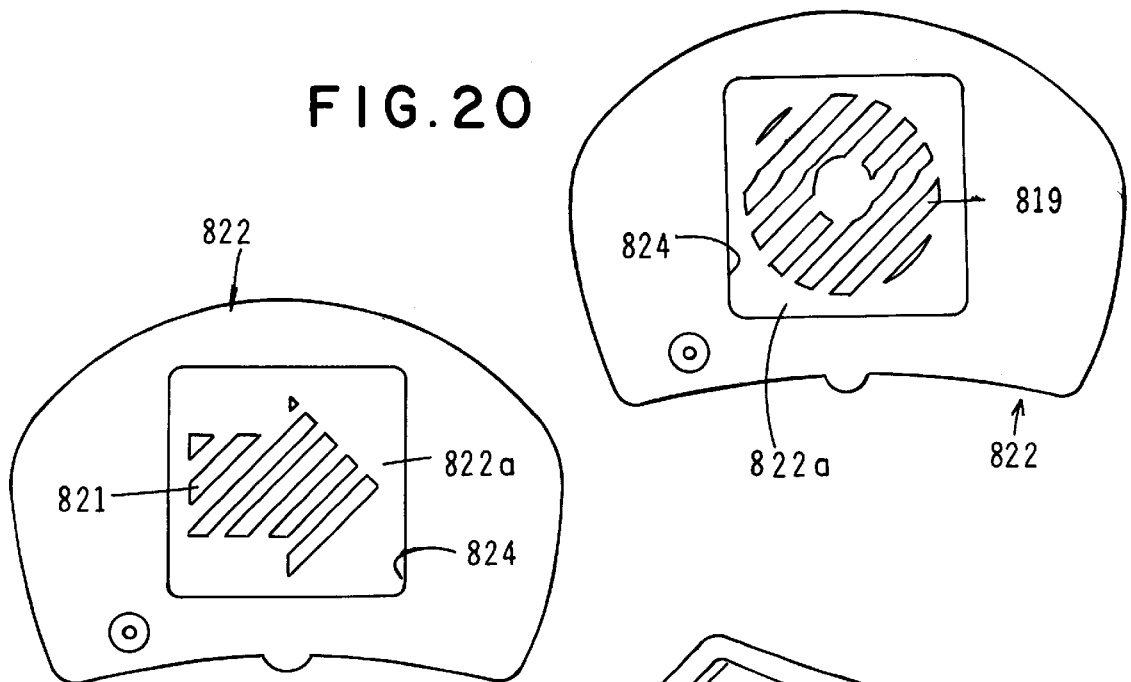
FIG. 20
FIG. 21
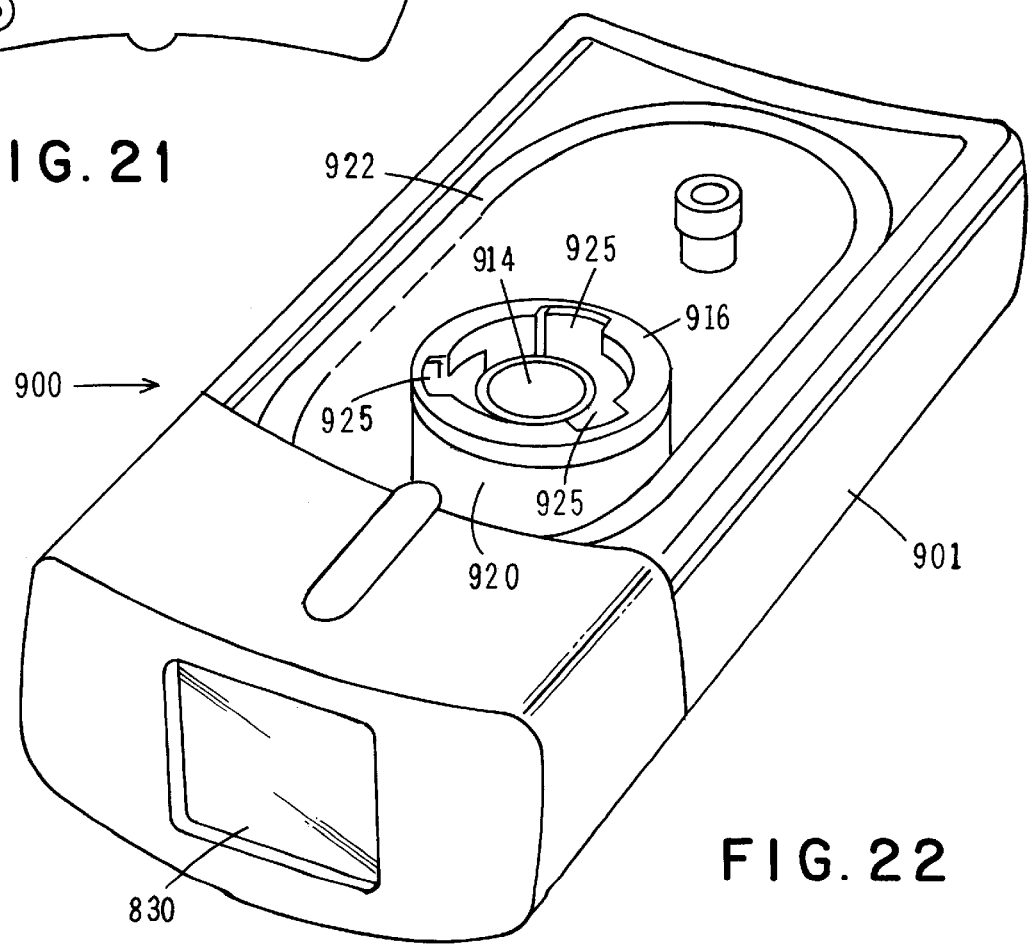
FIG. 22

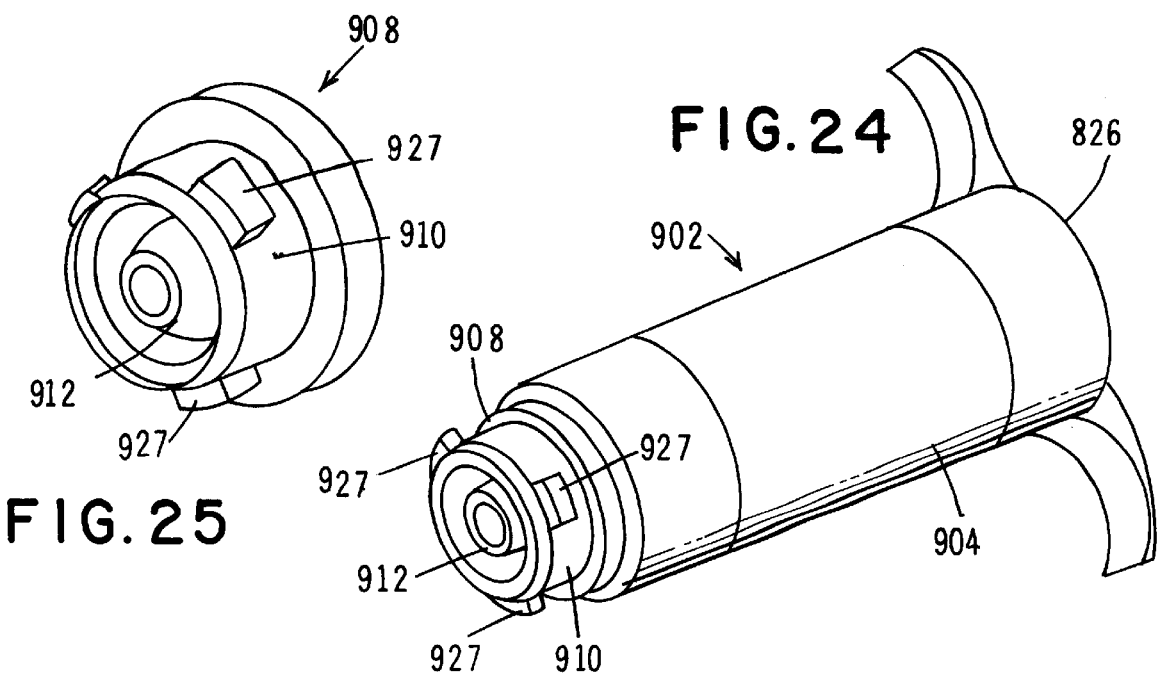
FIG. 24
FIG. 25
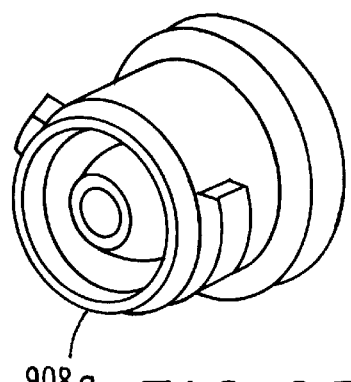
FIG. 25A
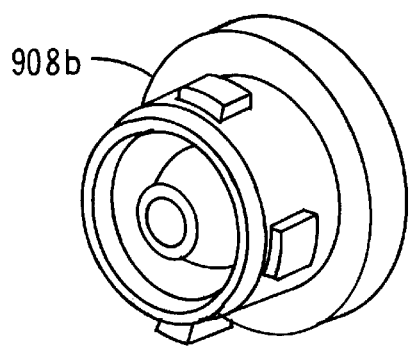
FIG. 25B
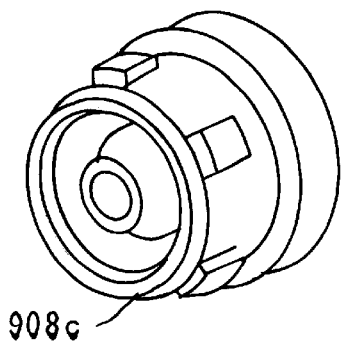
FIG. 25C
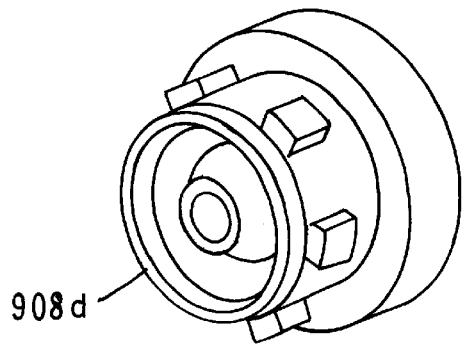
FIG. 25D

FLUID DELIVERY APPARATUS WITH RESERVOIR FILL ASSEMBLY

BACKGROUND OF THE INVENTION

This is a Continuation-in-Part Application of application Ser. No. 09/017,047 filed Feb. 2, 1998 now U.S. Pat. No. 5,962,794 which is a Continuation-In-Part of Ser. No. 08/718,686 filed Sep. 24, 1996, now U.S. Pat. No. 5,721,382, which is a Continuation-In-Part of application, Ser. No. 08/432,220, filed May 1, 1995, now abandoned.

FIELD OF THE INVENTION

The present invention relates generally to fluid delivery devices. More particularly, the invention concerns an improved apparatus, including a fluid dispenser having visual flow indicator means, for infusing medicinal agents into an ambulatory patient at specific rates over extended periods of time and a novel reservoir fill assembly for controllably filling the reservoir of the fluid dispenser.

DISCUSSION OF THE INVENTION

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Stich bladdery, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. U.S. Pat. No. 5,721,382 also issued to the present inventors on Feb. 24, 1998 also describes various alternate constructions and modified physical embodiments of the invention including the provision of a novel fluid actuated indicator means for visually indicating fluid flow from the device. This latter U.S. Pat. No. 5,721,382 is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's clothing or to the patient's body and can be used for the continuous infusion of antibiotics, hormones, steroids, blood clotting agents, analgesics including morphine, and like medicinal agents. Similarly, the devices can be used for I-V chemotherapy and can accurately deliver fluids to the patient in precisely the correct quantities and at extended microfusion rates over time.

SUMMARY OF THE INVENTION

It is an object of the present invention to provide an apparatus for delivering fluids at a precisely controlled rate which comprises a fluid dispensing component having a fluid reservoir for containing the fluids to be delivered and a reservoir fill component which can be removably interconnected with the fluid dispensing component. More particularly, it is an object of the invention to provide such an apparatus in which the reservoir fill component can be used to controllably fill the reservoir of the dispensing component and in which the dispensing component can be used for the precise infusion of pharmaceutical fluids to an ambulatory patient at controlled rates.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use using the novel reservoir fill component which can be removably interconnected to the lower surface of the base of the fluid dispenser.

Another object of the invention is to provide an apparatus as defined in the preceding paragraph in which the reservoir fill assembly is uniquely designed to accept a vial component of conventional construction which is factory filled with the medicinal fluid to be delivered to the patient.

A further object of the invention is to provide an accurate and highly reliable fluid delivery device which can be manufactured inexpensively in large volume by automated machinery.

Another object of the invention is to provide a device of the character described in which the dispenser component embodies a highly novel fluid flow indicator that provides a readily discernible visual indication of fluid flow status through the device.

Another object of the invention is to provide a device of the character described in which the dispenser component includes a novel infusion means in the form of delivery line assembly, which can be interconnected with the dispenser.

Another object of the present invention is to provide a fill assembly of the type described in the preceding paragraph in which the container of the container subassembly is partially received within a novel adapter subassembly that can readily be removably interconnected with the fluid dispensing device.

Another object of the invention is to provide a novel reservoir fill assembly for use with the fluid dispenser subassembly of the apparatus which is easy to use, is inexpensive to manufacture, and one which maintains the container in a substantially aseptic condition until time of use.

Other objects of the invention are set forth in U.S. Pat. Nos. 5,205,820 and 5,721,382 which are incorporated herein by reference and still further objects will become more apparent from the discussion which follows.

By way of summary, the fluid delivery apparatus of the present form of the invention comprises two cooperating assemblies, namely a fluid delivery apparatus or dispenser and a reservoir fill assembly which can be removably coupled with the lower surface of the base of the fluid dispenser for filling the fluid reservoir of the fluid dispenser. The fluid dispenser, which readily lends itself to automated manufacture, is generally similar to that described in U.S. Pat. No. 5,721,382 and includes a base and a stored energy means comprising at least one distendable elastomeric membrane which cooperates with the base to form a fluid reservoir. The fluid dispenser includes a highly novel fluid flow indicator means which comprises a mechanical fluid flow indicator that provides a clear visual indication of normal fluid flow and absence of fluid flow from the fluid reservoir. The reservoir fill assembly also uniquely comprises two cooperating components, namely a fluid container assembly and an adapter assembly. The adapter assembly functions to connect the reservoir fill assembly to the fluid dispenser.

BRIEF DESCRIPTION OF THE DRAWINGS

FIG. 8 is a generally perspective, exploded view of an alternate form of the reservoir fill assembly.

FIG. 9 is a generally perspective view of the alternate form of reservoir fill assembly mated with the fluid delivery apparatus.

FIG. 12 is a fragmentary, cross-sectional view of an alternate form of container and adapter assembly of the apparatus of the invention.

FIG. 13 is an exploded, cross-sectional view of an alternate form of plunger connector subassembly adapted to house an alternate form of flow control means for controlling fluid flow toward the fluid dispenser assembly.

FIG. 18 is an enlarged cross-sectional view taken along lines 18—18 of FIG. 16.

FIG. 20 is a front view of the fluid dispenser showing flow indicator indicia indicating no flow of fluid through the apparatus.

FIG. 21 is a front view of the fluid dispenser showing the flow indicator indicia indicating fluid flow through the apparatus.

FIG. 22 is a generally perspective view of an alternate form of fluid dispenser component of the present invention.

FIG. 24 is a generally perspective view of an alternate form of fill assembly of the invention for use with the fluid dispensing component shown in FIG. 22.

FIG. 25 is a generally perspective view of the forward portion or cap assembly of the fill assembly shown in FIG. 24.

FIG. 25A is an alternate form of the forward portion or cap assembly of the fill assembly shown in FIG. 24.

FIG. 25B is still another form of forward portion of the fill assembly shown in FIG. 24.

FIG. 25C is yet another embodiment of the forward portion of the fill assembly shown in FIG. 24.

FIG. 25D is yet another form of the forward portion of the fill assembly shown in FIG. 24.

DESCRIPTION OF THE INVENTION

Figure 1:
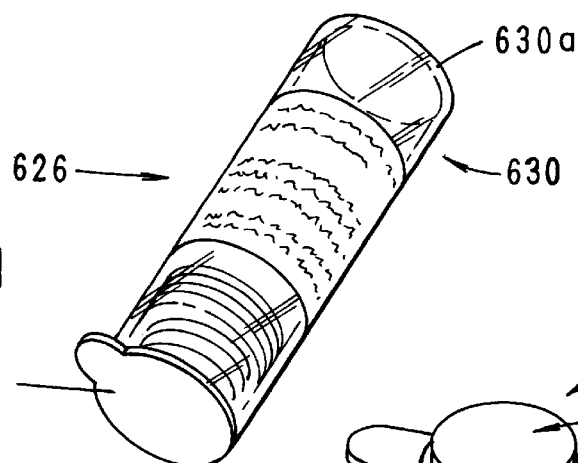
FIG. 1 is a generally perspective exploded view of one form of the reservoir fill assembly of the invention.
Figure 2:
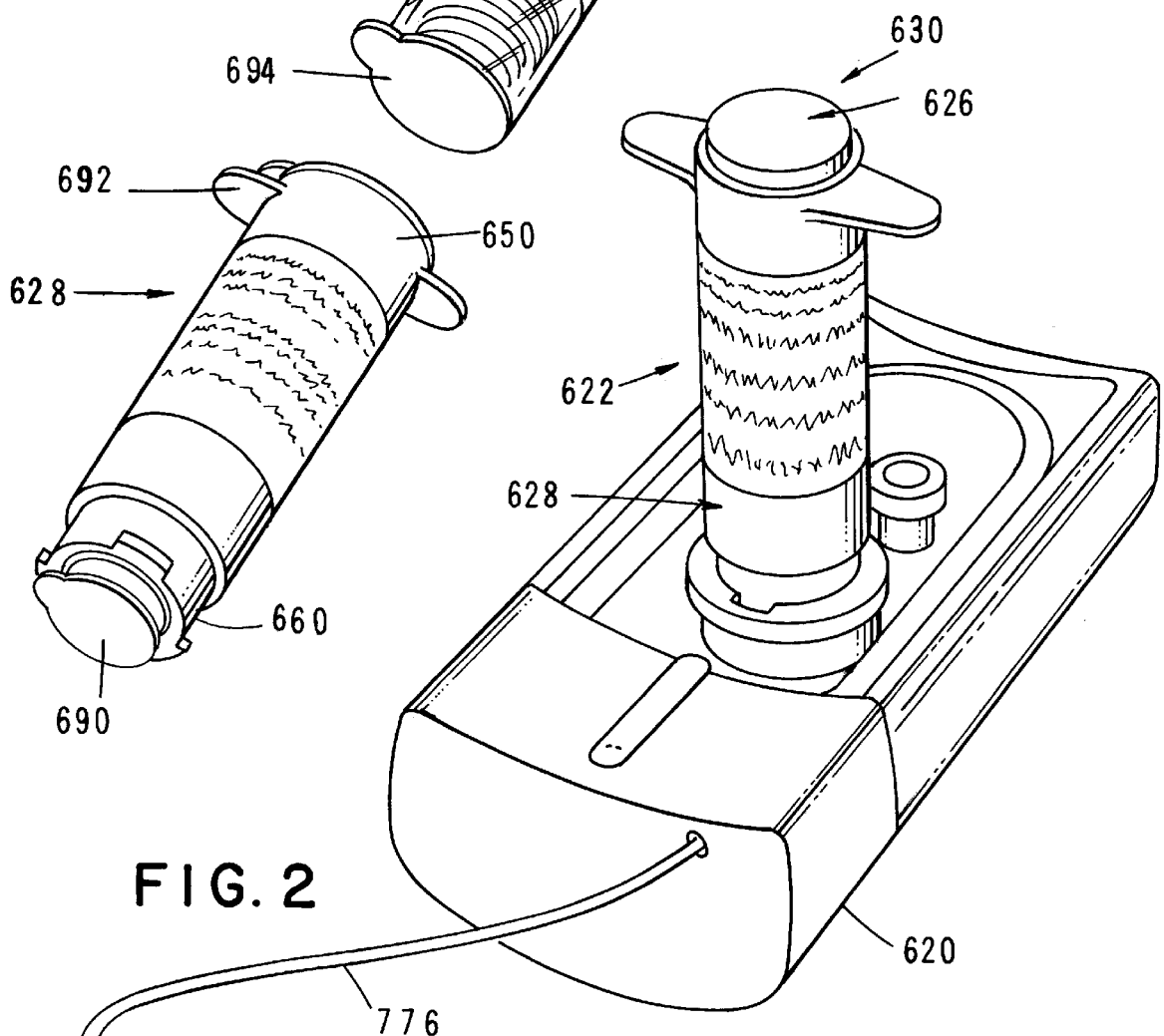
FIG. 2 is a generally perspective, bottom view of one form of the fluid dispenser of the invention showing the reservoir fill assembly connected thereto.

Referring to the drawings and particularly to FIGS. 1 through 4, one form of the apparatus of the present invention is there illustrated. As best seen in FIGS 1 and 2, the apparatus here comprises two major cooperating assemblies, namely a fluid dispensing apparatus or fluid dispenser 620 and a reservoir fill assembly 622 which can be operably coupled with fluid dispenser 620. As will be described in greater detail hereinafter, dispenser 620 is made up of two major cooperating subassemblies namely, a reservoir subassembly and an infusion means for infusing medicinal fluids into the patient.

Figure 3:
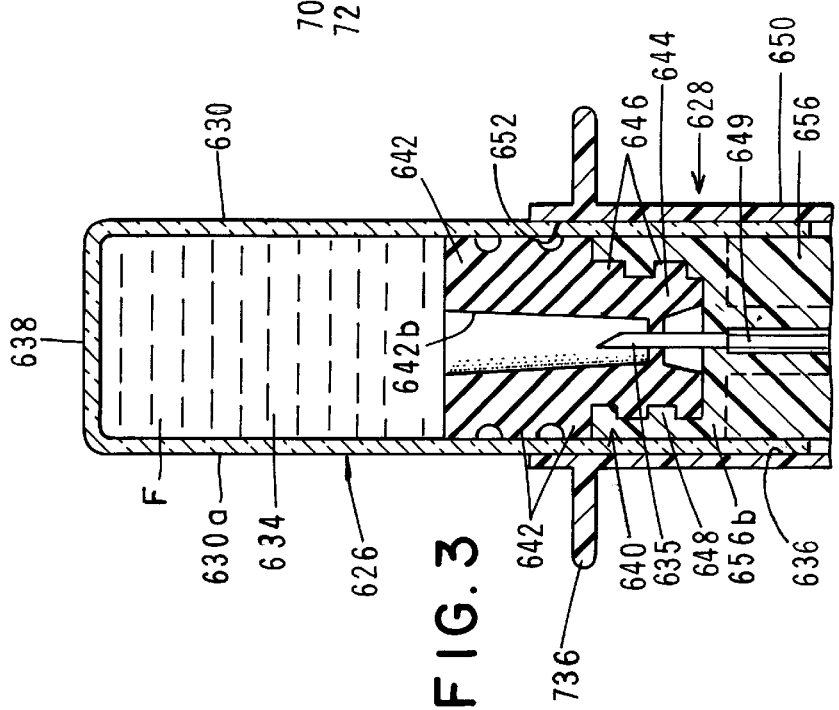
FIG. 3 is a left-side elevational, cross-sectional view of the assembly shown in FIG. 1.

Turning particularly to FIGS. 1 and 3, the novel reservoir fill assembly 622 of the invention can be seen to also comprise two major components, namely a container subassembly 626 (FIG. 1) and an adapter subassembly 628. Container subassembly 626 includes a container 630 which contains the medicinal fluid with which the reservoir of the dispensing apparatus is to be filled. When interconnected with the dispensing apparatus, the adapter subassembly 628 permits transfer from container 626 to the reservoir 632 of the dispenser component.

As best seen in FIG. 3, container 630 includes a body portion 630a, having a fluid chamber 634 for containing an injectable fluid "F". Body portion 630 is provided with a first open end 636, and a second closed end 638. First open end 636 is sealably closed by closure means here provided in the form of a plunger assembly 640. Plunger assembly 640 comprises an elastomeric plunger 642 and a connector means, or connector 644 which functions to interconnect the container assembly with the adapter assembly. Plunger assembly 640 is telescopically movable within chamber 634 of container subassembly 626 from a first location proximate first open end 636 to a second location proximate second closed end 638.

Connector 644 includes threads 646 which can be threadably connected to threads 648 provided on adapter assembly 628. Connector 644 also includes a pierceable central wall 644a which is pierceable by an elongated cannula 635 of the adapter assembly, which cannula comprises a part of the first flow control means of an adapter assembly for controlling fluid flow toward the fluid dispenser. Cannula 635 is insert molded into a pusher means and includes a central fluid flow passageway 649. Connector 644 is connected to plunger 642 in the manner shown in FIG. 3 so that as plunger 642 is moved toward closed end 638, in a manner presently to be described, connector 644 and plunger 642 will move as a unit. To prevent leakage of fluid past plunger 642, the plunger is provided with rings 642a which are of a diameter slightly greater than the inside diameter of container body 630a. Plunger 642 also includes a central fluid passageway 642b which is in open communication with fluid chamber 634.

Adapter assembly 628 comprises a hollow housing 650 having a first open end 652 and a second closed end 654. Container assembly 626 is telescopically receivable within open end 652 of housing 650 in the manner shown in FIG. 3 so that the housing can be moved from the first extended position shown in FIG. 3 to a second container encapsulation position wherein container 630 is substantially encapsulated within housing 650. Provided interiorly of the adapter subassembly is the previously mentioned pusher means which is shown here as a pusher body 656. Pusher body 656, which is generally cross shaped in configuration and functions to support cannula 635 and to move plunger 642 within fluid chamber 634 from the first forward position shown in FIG. 3 to a second position wherein it is disposed proximate end wall 638. Pusher body 656 also includes a head portion 656b within which threads 648 are formed. End wall 654 of housing 650 is provided with a fluid outlet 654a which comprises a part of the second flow control means of the invention for permitting fluid flow toward the delivery apparatus of the invention.

Also forming a part of the adapter assembly of the invention is a closure cap assembly 660 (FIG. 4) which is connected to body portion 650 in the manner shown in FIG. 3. Cap assembly 660 includes a generally cylindrical exterior wall defining a band-like portion 662 and an internal dividing wall 664 which cooperates with wall 662 to form first and second chambers 666 and 668. Connected to wall 664 and extending into chamber 666 is a cannula 670, the purpose of which will presently be described. Disposed within chamber 668 is one of the valving means of the invention which here comprises a conventional umbrella type valve assembly 672 which functions to control fluid flow from passageway 649 toward the central fluid passageway of cannula 670 via a passageway 674 formed in dividing wall 664. Valve assembly 672 is of a conventional configuration having a central hub-like portion which is received within a central bore provided in a support plate 676 and a circumferentially extending, resiliently deformable, umbrella shaped flow control skirt 678 which is deflected outwardly by fluid flowing through passageway 649 so as to permit flow into passageway 674 of dividing wall 676.

Turning next to FIGS. 8 and 9, an alternate form of adapter assembly is there shown and generally identified by a numeral 680. Adapter assembly 680 is similar in construction to assembly 628, but includes a pair of interconnected, side-by-side hollow bodies 682, each of which is of the same general construction as the previously described hollow body 650. Each of the hollow bodies 682 has an outlet which permits fluid flow toward an umbrella type valve which is identical to valve 672. Fluid flowing through either of the valves 672 will flow into a central fluid passageway formed in a central connector 684 which interconnects the two hollow housings 682 and then on to the fluid delivery device 620.

As depicted in FIG. 8, adapter assembly 680 is adapted to receive a pair of container assemblies 626 which are of the character previously described. Each of the container assemblies can contain an injectable medicament of either the same or a different character for introduction into the reservoir of the particular delivery assembly which is selected to deliver the medicament to the patient.

Prior to use, the adapter assembly components 632 and 684 of the reservoir fill assembly is maintained in a protected and substantially sterile configuration by tear-away end caps 690 and 692 (see FIG. 8). As indicated in FIGS. 1 and 8, a tear-away end cap 690 is receivable over and closes the forward end of adapter assembly 680, while tear-away end cap 692 is received over and closes the rearward open end portion of bodies 650. Similarly, as shown in FIGS. 1 and 8, a tear-away cap 694 is received over and closes the open ends of the container assemblies 626.

Turning again to FIGS. 1 through 4, the fluid delivery or dispenser assembly 620 of the apparatus of this form of the invention is similar in some respects to that described in incorporated by reference U.S. Pat. No. 5,721,382 and includes a housing assembly comprising a base 698, a capture ring 699, a stored energy source, or distendable membrane 700 and a cover 702 for enclosing the stored energy source, the capture ring and the base. Base 698 includes an ullage defining protuberance 704 and a membrane capture portion 706. Disposed between base 698 and cover 702 is the membrane capture ring 699 which has a bottom opening 699a which receives protuberance 704 of base 698 (see FIG. 3).

Figure 4:
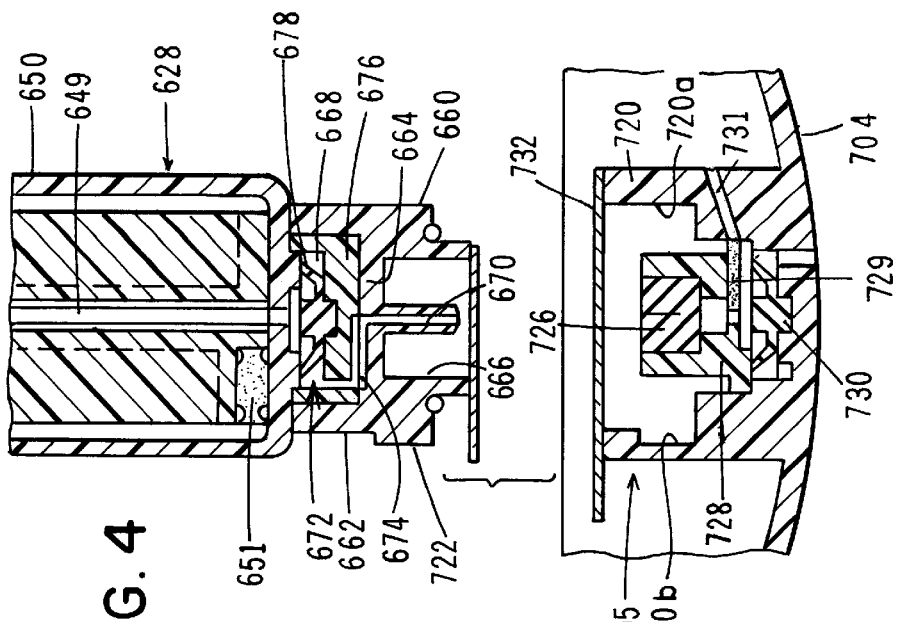
FIG. 4 is a fragmentary, cross-sectional view of the lower portion of the fill adapter assembly ready to be mated with the connector subassembly of the fluid delivery device portion of the apparatus shown in FIG. 1.

As shown in FIGS. 3 and 4, base 698 comprises, in addition to the distendable member engaging protuberance, or ullage 704, a novel dispenser connector subassembly 705, to which the reservoir fill assembly 622 is interconnected in the manner shown in FIG. 2. Base 698 also includes an upstanding tongue 698b which extends about the perimeter of the base and is closely receivable within a groove 699b formed in the capture ring 699 (FIG. 3). When the base 698 and the membrane capture ring 699 are assembled in the manner shown in FIG. 3, the periphery of distendable membrane 700 will be securely clamped within groove 699b by tongue 698b. After the parts are thusly assembled, base 698 is bonded to capture ring 699 by any suitable means such as sonic bonding which also functions to simultaneously trim membrane 700. This done, cover 702 is mated with capture ring 699 in the manner shown in the drawings and is suitably bonded in place. Cover 702 can, if desired, be constructed from a substantially transparent plastic material which is impermeable to fluids, including gases.

During the reservoir filling step, the details of which will presently be described, fluid under pressure will flow into inlet passageway 710 of the fluid dispenser via a conventional umbrella valve 730 and thence into reservoir 632 which is formed between protuberance 704 and the stored energy membrane 700. As the fluid under pressure flows into the reservoir, it will cause membrane 700 to distend outwardly from protuberance 704 so as to build up internal stresses within the membrane. While the stored energy means can be in the form of a single prestressed or unstressed isotropic, elastomeric distendable membrane, such as membrane 700, it can also be constructed as a laminate assemblage made up of a plurality of initially generally planar distendable elements of films. Such constriction is described in U.S. Pat. No. 5,721,382, which application is incorporated herein by reference. During the infusion step, the internal stresses formed in membrane 700 will cause it to move toward protuberance 704 and fluid within reservoir 632 will be uniformly and controllably forced outwardly through a passageway 714 and then through a passageway 716 formed in base 698 in a direction toward the infusion means of the invention.

In using the apparatus of this form of the invention, seal cap 694 is removed from container assembly 626 and the open end of container 630 is inserted into the open end of adapter body 650 in the manner shown in FIG. 3. As connector member 644 is threadably interconnected with pusher 656 cannula 635 will pierceably engage and penetrate central wall 644a of the connector thereby opening fluid communication between fluid chamber 634 of the container assembly and passageway 649 of the pusher assembly member 656. Once wall 644a has been penetrated, an inward force exerted on container assembly 626 will cause body 656 to urge plunger 642 inwardly of container reservoir 634 from a first location proximate open end 636 to a second location proximate closed end 638. As plunger 642 moves inwardly, fluid within reservoir 634 will be free to flow into the central fluid passageway of cannula 635 and toward adapter assembly passageway 649. Any gases trapped within passageway 649 will vent to atmosphere via a hydrophobic vent element 651 which connects passageway 649 with an elongated annular passageway formed between the outer surface of container 630 and the inner surface of housing 650. Gases flowing into passageway 733 will leak past container 630 to atmosphere.

To interconnect the reservoir fill assembly with the fluid delivery apparatus 620, the forward end of the adapter assembly is inserted into a hub like portion 720 which comprises a part of connector assembly 705 and defines a receiving chamber 720a. Portion 720 is integrally formed with protuberance 704 (FIG. 4) and includes circumferentially spaced openings 720b which are adapted to receive bayonet type connector ears 722 formed on cap assembly 660 (FIGS. 3 and 4). Relative rotation of the fill assembly 622 and the fluid delivery apparatus 620 will securely interconnect the components in the manner shown in FIG. 3. As indicated in FIG. 3, as the fill assembly is mated with the delivery component, cannula 670 of the adapter assembly will pierce a pierceable septum 726 which is mounted within septum mounting component 728 which is disposed within hub 720 that forms a part of the connector assembly 705 (see FIG. 4). Also disposed within hub 720 is a vent means shown here as a hydrophobic vent element 729 and delivery component valving means for controlling fluid flow toward inlet 710. This delivery component valving means here comprises a conventional umbrella type check valve 730 which permits fluid flow from cannula 670 toward passageway 710, but blocks fluid flow in the opposite direction. Valve 730 is similar in construction and operation to the previously described umbrella valve 672.

After the peelable end cap 732 (FIG. 4) of the fluid delivery assembly 620 has been removed and the fill assembly 622 has been mated therewithin, the assemblage thus formed can be interconnected with the delivery assembly in the manner previously described. Fluid can be expelled from the fluid chamber 634 of the container assembly into the fluid reservoir 632 of the fluid delivery apparatus 620. This step is accomplished by urging container 630 into the annular space 733 defined by the interior wall of hollow housing 650 and the exterior surface of adapter body 656. This is accomplished by gripping finger engaging ears 736 (FIG. 3) and then urging the container 630 inwardly with the thumb. During the filling step, any air trapped within passageway 649 will be vented to atmosphere via vent element 651 and annular space 733. Similarly, any air trapped within septum mounting component 728 will be vented to atmosphere via a hydrophobic vent element 729 and a vent passageway 731 formed in connector assembly 705.

As shown in FIG. 3, the fluid dispenser also includes fluid recovery means for recovering fluid from reservoir 632. This important means, which enables recovery at any time of fluid contained within the reservoir, here comprises a septum 737 housed within a chamber 737a formed in protuberance 704. Septum 737 is pierceable by a cannula of a conventional syringe assembly that can be used to remove fluid from the reservoir.

As previously mentioned, after the reservoir filling step and during the fluid dispensing step, the prestressed membrane 700 will tend to return toward a less distended configuration causing fluid within reservoir 632 to flow outwardly of the reservoir into passageway 714 and then into passageway 716. The fluid under pressure will next flow into passageway 740 of the inlet port of disk shaped member 742 (see FIGS. 6, 7, 10 and 11). Member 742 is similar in construction and operation member 466 shown in FIG. 62 and mates with a support structure 746 which is similar in form to support structure 456 (FIG. 61).

Figure 5:
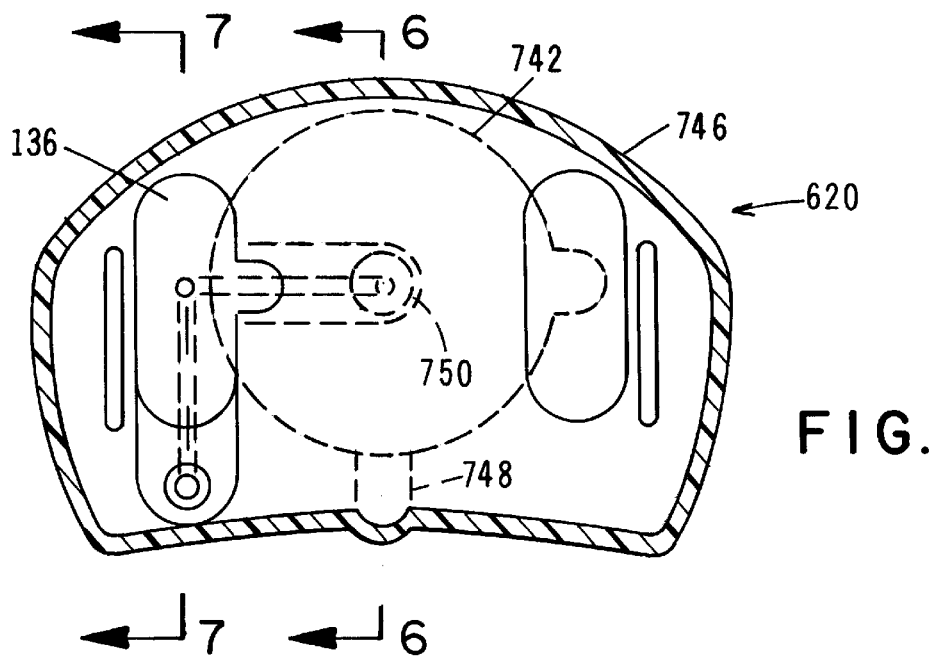
FIG. 5 is a cross-sectional view taken along lines 5—5 of FIG. 3.

Member 742 includes a downwardly extending fluid inlet leg or segment 748 (FIG. 5) which is provided with the previously identified fluid passageway 740. As shown in FIG. 3, passageway 740 is adapted to communicate with reservoir 632 of the dispenser via passageways 714 and 716 when member 742 is mated with support structure 746 in the manner indicated in FIGS. 3 through 7.

Figure 10:
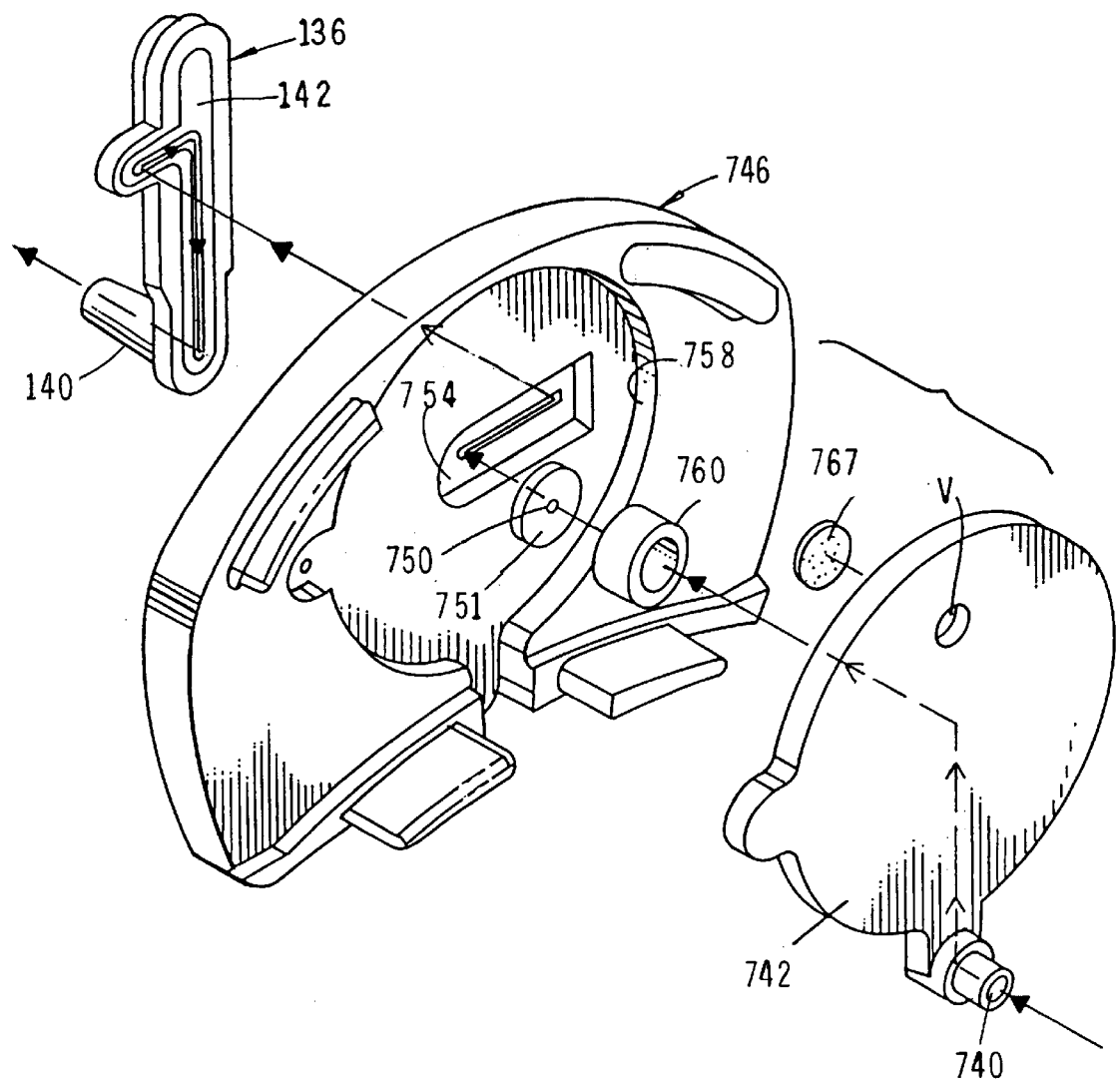
FIG. 10 is a generally perspective, exploded rear view of the forward portion of the fluid dispenser which houses the flow rate control means of the invention.
Figure 11:
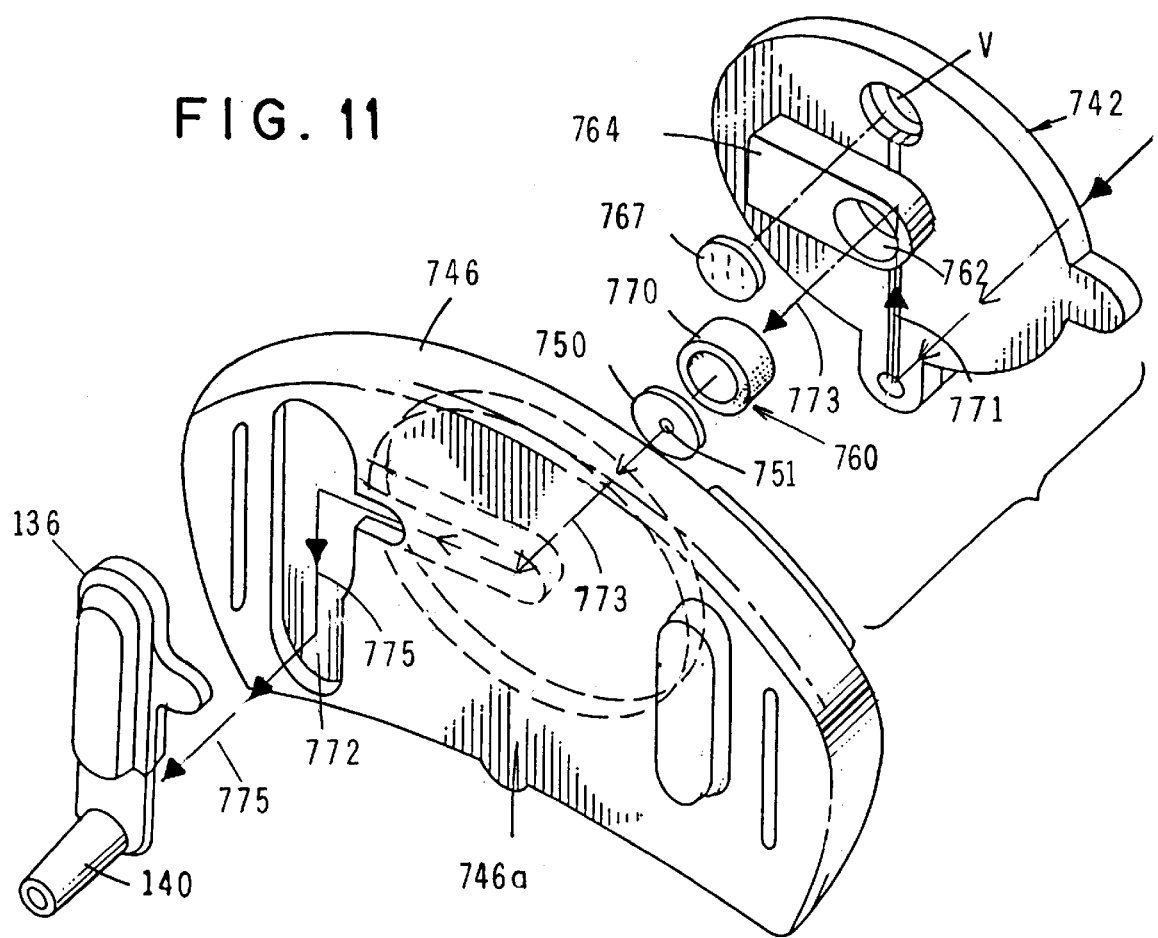
FIG. 11 is a generally perspective, exploded front view of the forward portion of the fluid dispenser.

Turning to FIGS. 10 and 11, an alternate form of dispenser flow control means is there shown. As before, these alternate dispenser flow control means function to control fluid flow outwardly of the device. The embodiment of the invention shown in FIGS. 10 and 11 comprises a first and second flow control means. First flow control means includes a fluid flow rate control wafer 750, which is closely received within a cavity 754. Wafer 750 is held in position within cavity 754 by a tube-like, elastomeric member 760 (FIGS. 10, 11, and 11a) which is receivable within a recess 762 formed in a boss 764 provided on a disc-like member 742 (FIG. 11). Member 742 is similar in many respects to member 116 which is shown in FIG. 21. However, the manifolding stand-offs 118 provided on member 116 have been replaced in member 742 with boss 764 which is provided with cavity 762. When member 742 is in place within cavity 758 of structure 746, wafer 750 is securely positioned between elastomeric sleeve 760 and the bottom wall of cavity 754. As before, a vent patch 767 vents to atmosphere any air trapped within the fluid passageways of the device via a vent "V".

Figure 11A:
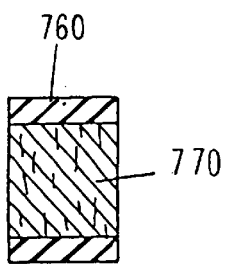

As best seen in FIGS. 10 and 11, the rate control wafer 750 which has a single laser drilled aperture 751 which controls fluid flow toward an assembly 136. Laser drilled wafer 750 can be constructed of metal, ceramic or like material and functions to precisely control fluid flow toward assembly 136 at a very precise rate. The second, or back-up flow control means here comprises a porous rate control frit 770 (FIG. 11a). Reference should be made to co-pending Ser. No. 09/017,047 for a description of assembly 136 and for a more detailed discussion of the various materials suitable for constructing various components of this alternate dispenser flow control means of the invention as described in the preceding paragraphs.

Figure 6:
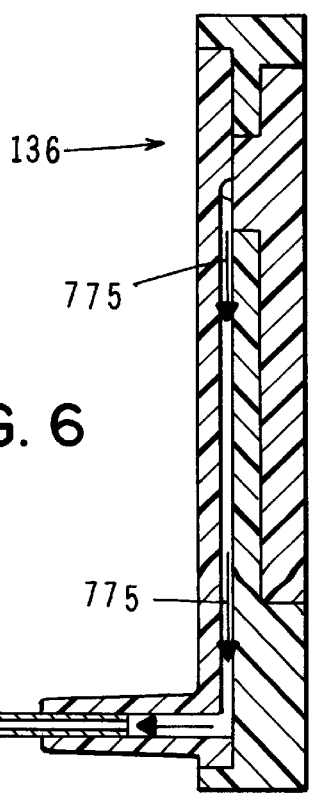
FIG. 6 is a cross-sectional view taken along lines 6—6 of FIG. 5.
Figure 7:
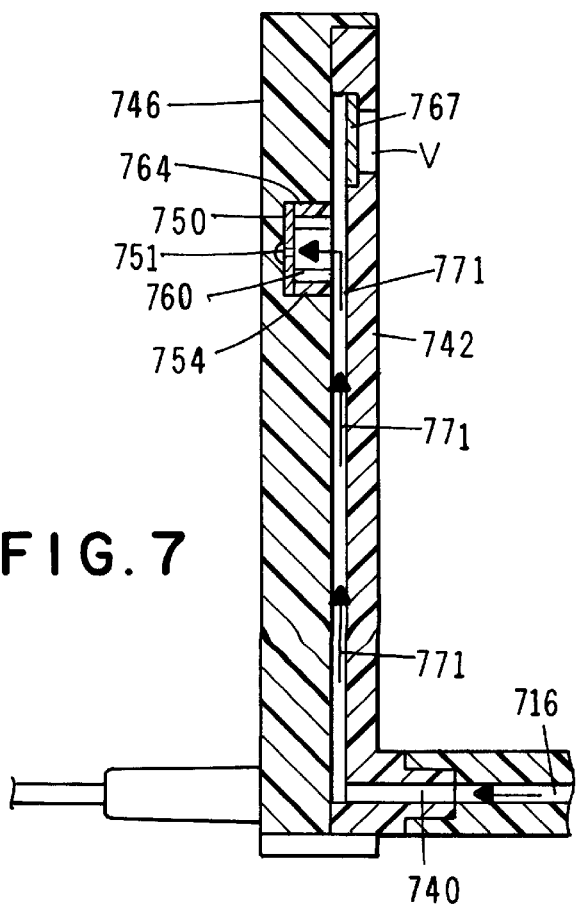
FIG. 7 is a cross-sectional view taken along lines 7—7 of FIG. 5.

With the construction described in the preceding paragraphs, when fluid is forced into passageway 714 by the stored energy means, the fluid will flow into passageway 716, then into passageway 740 of member 742 and finally in the direction of arrows 771 into chamber 762 formed in boss 764 (see FIGS. 6 and 11). The fluid under pressure will then flow through frit 770 toward the fluid outlet port of the flow control subassembly. As previously mentioned, the outlet port comprises the uniquely shaped assembly 136 which is receivable in a cavity 772 formed in the back or downstream wall 746a of a substrate 746. Assembly 136 includes a fluid outlet 140 and an internal chamber 142 (FIG. 10). As indicated in FIGS. 7 and 11, fluid flowing into chamber 772 will flow downwardly in the direction of the arrows 775 toward outlet 140 and into the infusion means of the apparatus.

Referring to FIG. 2, one form of infusion means of the apparatus of the invention for delivering fluid from the dispenser component to the patient is there illustrated and generally designated by the numeral 774. This infusion means, or delivery line assembly, is interconnected with outlet 140 of the dispenser component of the apparatus of the invention in the manner shown in FIGS. 2 and 7. A long length of tubing 776 interconnects outlet 140 with a luer fitting 778 which is of a conventional construction. Intermediate the ends of length of tubing 776 is a gas vent and filter 779 which is also of a conventional construction and a tubing clamp 780 which is also of a character well known to those skilled in the art and functions to block fluid flow through tubing 776 (FIG. 2).

Referring to FIGS. 12 and 13, an alternate form of reservoir fill assembly is there illustrated. This assembly is generally similar to assembly 622 and like numbers are used in FIGS. 12 and 13 to identify like components. As before, the reservoir fill assembly comprises two major components, namely a container subassembly and an adapter subassembly. The container subassembly includes a container 630 which contains the medicinal fluid with which the reservoir of the dispensing apparatus is to be filled. Container 630 is provided with a first open end 636, and a second closed end 638. First open end 636 is sealably closed by closure means here provided in the form of a plunger assembly 781 which is of a somewhat different construction from plunger assembly 640. This plunger assembly 781 here comprises an elastomeric plunger 783 and a connector means, or connector 785 which functions to interconnect the container assembly with the adapter assembly. As before, the plunger assembly is telescopically movable within container 630 from a first location proximate first open end 636 to a second location proximate second closed end 638.

Unlike connector 644, connector 785 does not include a pierceable central wall which is pierceable by the elongated cannula 634 of the adapter assembly. Rather the central wall has been eliminated and fluid flow from container 630 toward the adapter assembly is controlled by an alternate flow control means, here provided as a valving means housed within plunger 783 in the manner shown in FIGS. 12 and 13. As shown in FIG. 13, plunger 783 includes a central chamber 783a which houses the valving means. This novel valving means here comprises a conventional umbrella type valve assembly 787 which functions to control fluid flow from a passageway 789a formed in valve capture member 789 toward a central fluid passageway 791 formed in the pusher means 793 of the modified adapter assembly of this latest embodiment (FIG. 12). Valve assembly 787 is of a conventional configuration having a central hub-like portion which is received within a central bore provided in a support plate 793 and a circumferentially extending, resiliently deformable, umbrella shaped flow control skirt 795 which is deflected outwardly by fluid flowing through passageway 789a so as to permit flow into passageway 785a of connector 785.

As in the earlier forms of the invention, the alternate form of adapter assembly shown in FIG. 12 has an outlet which permits fluid flow toward an umbrella type valve which is identical to valve 672. Fluid flowing through valve 672 will flow into a fluid passageway formed in a central connector 664 and then into reservoir 632 via a second umbrella valve 730 (see, for example FIG. 3).

Figure 14:
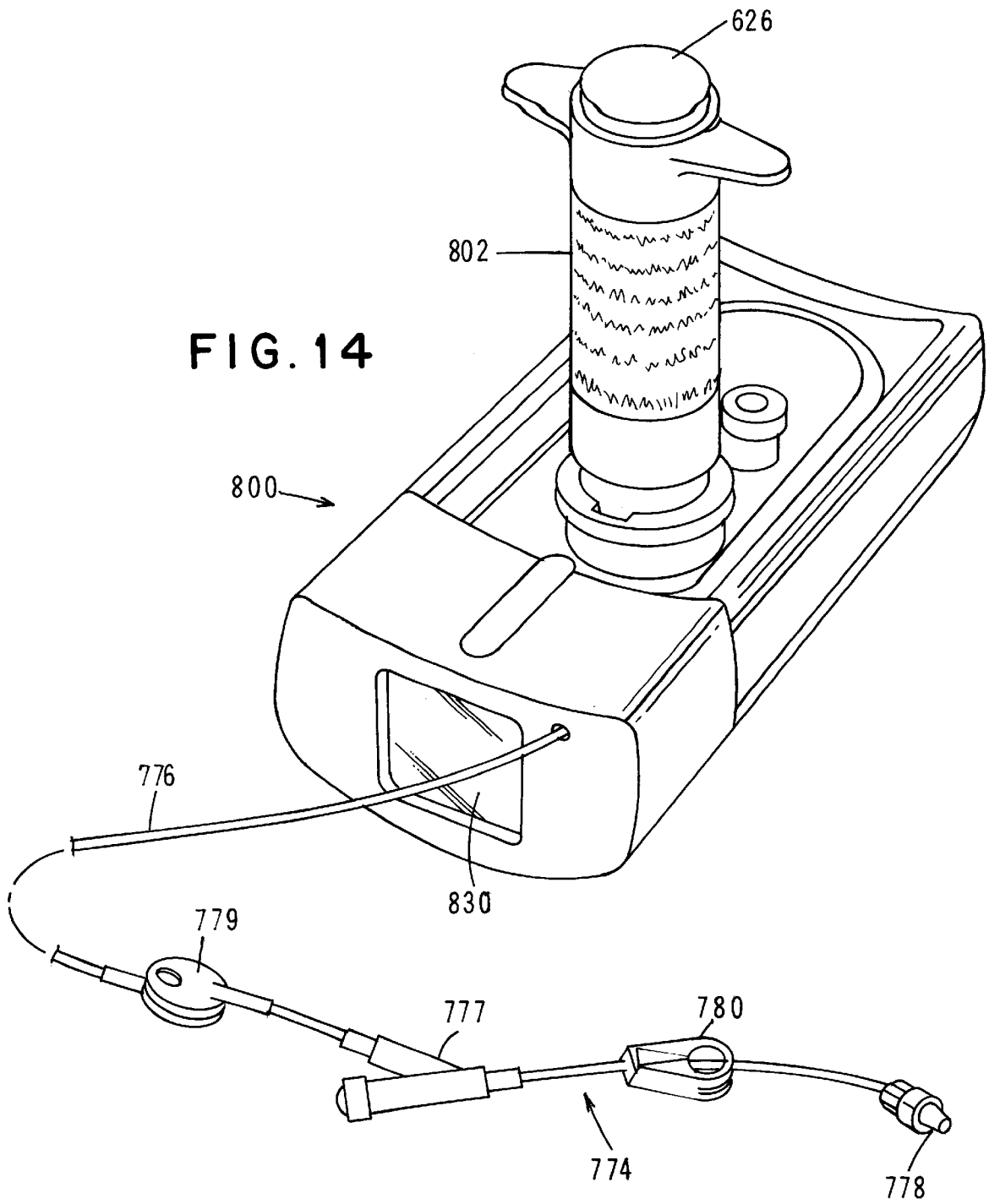
FIG. 14 is a generally perspective, bottom view of an alternate form of the fluid dispenser of the invention showing the reservoir fill assembly connected thereto.

Turning now to FIGS. 14 through 21, an alternate form of the fluid delivery apparatus of the present invention is there illustrated. This apparatus is similar in many respects to that shown in FIGS. 1 through 3 and like numerals are used to identify like components. As best shown in FIG. 14, as before the apparatus comprises two major cooperating assemblies, namely a fluid dispensing apparatus or fluid dispenser 800 and a reservoir fill assembly 802 which can be operably coupled with fluid dispenser 800. Reservoir fill assembly 802 is very similar in construction and operation to that previously described herein. Dispenser 800, on the other hand, is made up of three major cooperating subassemblies namely, a reservoir subassembly, a fluid flow indicator means and an infusion means for infusing medicinal fluids into the patient.

Figure 15A:
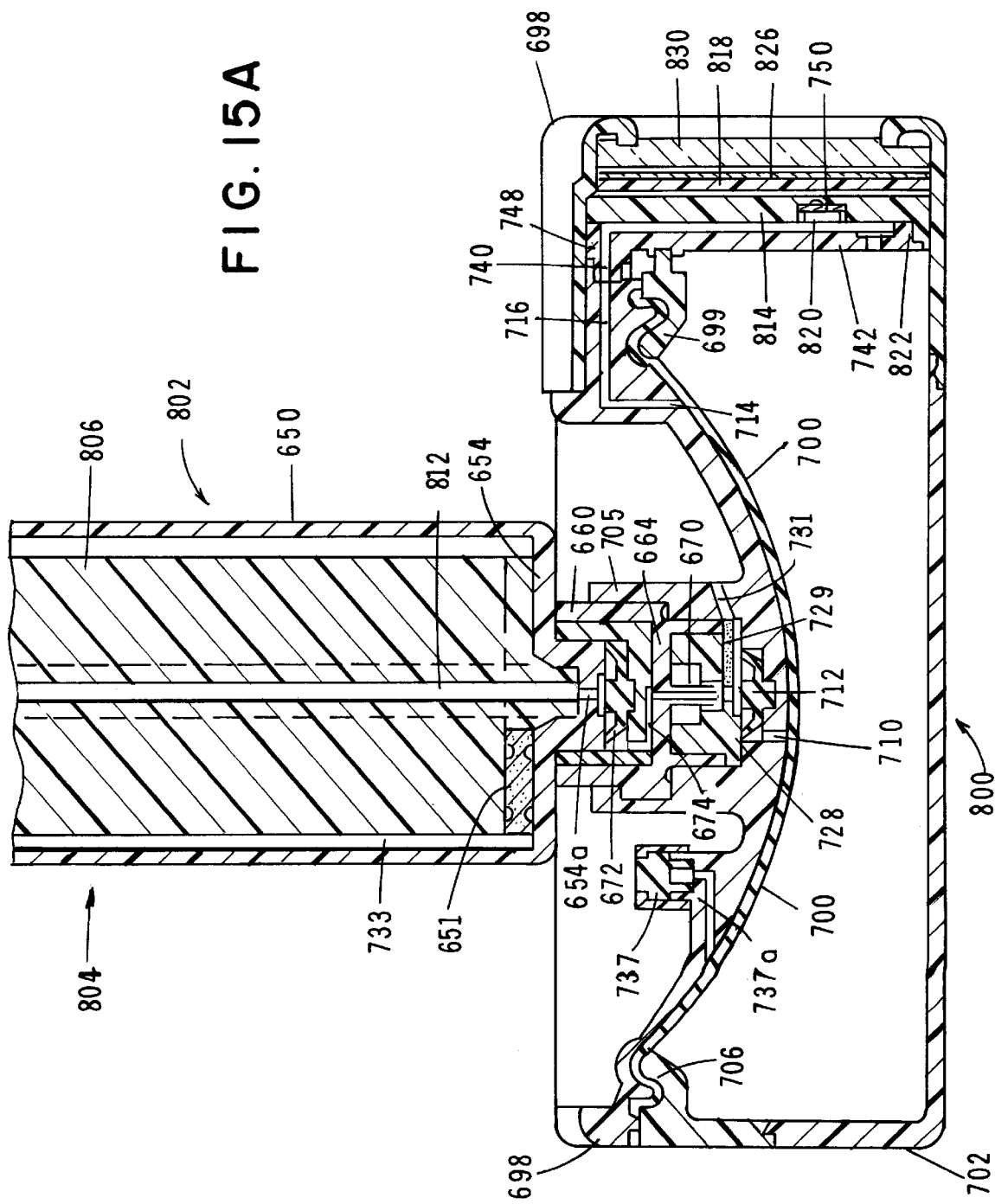
FIG. 15 is a cross-sectional view of the alternate form of the fluid dispenser shown in FIG. 14 but showing the reservoir fill assembly in a starting position prior to filling the reservoir of the dispensing component.

As shown in FIG. 15, reservoir fill assembly 802 comprises two major components, namely a container subassembly 626 and an adapter subassembly 804. Container subassembly 626 is identical in construction and operation to that previously described and contains the medicinal fluid with which the reservoir of the dispensing apparatus is to be filled. When interconnected with the dispensing apparatus, the adapter subassembly 804, which is of a slightly different configuration permits fluid transfer from container 626 to the reservoir of the dispenser component.

As best seen in FIG. 15, container 630 includes a body portion 630a, having a fluid chamber 634 for containing an injectable fluid "F". Body portion 630 is provided with a first open end 636, and a second closed end 638. First open end 636 is sealably closed by closure means here provided in the form of a plunger assembly 640.

Adapter assembly 802 comprises a hollow housing 650 having a first open end 652 and a second closed end 654. Container assembly 626 is telescopically receivable within open end 652 of housing 650 in the manner shown in FIG. 15 so that the housing can be moved from the first extended position shown in FIG. 15 to a second container encapsulation position wherein container 630 is substantially encapsulated within housing 650. Provided interiorly of the adapter subassembly is a pusher means which is of slightly different construction from that previously described. More particularly, the pusher means here comprises a pusher body 806 which is generally cross shaped in configuration and functions to support cannula 810 and to move plunger 640 within fluid chamber 634 from the first forward position shown in FIG. 15 to a second position wherein it is disposed proximate end wall 638.

Needle-like cannula 810, unlike blunt end cannula 644 has a sharp piercing end 810a which is adapted to pierce wall 644a of the plunger assembly to place fluid chamber 634 of the container into fluid communication with an elongated fluid passageway 812 formed in pusher body 806. Passageway 812 communicates with fluid outlet 654a formed in end wall 654 and comprises a part of the second flow control means of the invention for permitting fluid flow toward the delivery apparatus of the invention. Once again, vent means, or hydrophobic element 651 is provided within body 650 to vent to atmosphere gases trapped within passageway 812.

Also forming a part of the adapter assembly of this latest form of the invention is a closure cap assembly 660 having a barrel-like portion which is connected to body portion 650 in the manner shown in FIG. 15. As before, cap assembly 660 includes an internal dividing wall 664 which supports piercing cannula 670. Disposed within cap assembly 660 is one of the valving means of the invention which, as before, comprises a conventional umbrella type valve assembly 672 of the character previously described which functions to control fluid flow from passageway 812 toward the central fluid passageway of cannula 670 via a passageway 674 formed in dividing wall 664.

As indicated in FIG. 15, the fluid delivery or dispenser assembly 800 of the apparatus of this latest form of the invention is similar in many respects to that shown in FIGS. 2 and 3 and earlier described herein. More specifically, assembly 800 includes a housing assembly comprising a base 698, a capture ring 699, a stored energy source, or distendable membrane 700 and a cover 702 for enclosing the stored energy source, the capture ring and the base. Base 698 includes an ullage defining protuberance 704 and a membrane capture portion 706. Disposed between base 698 and cover 702 is the membrane capture ring 699 which functions in the manner previously described to capture membrane 700. As before, base 698 comprises dispenser connector subassembly 705, to which the reservoir fill assembly is interconnected in the manner previously described.

During the reservoir filling step of this latest form of the invention,fluid under pressure will flow into inlet passageway 710 of the fluid dispenser via a conventional umbrella valve 712 and thence into the reservoir which is formed between protuberance 704 and the stored energy membrane 700. As the fluid under pressure flows into the reservoir, it will cause membrane 700 to distend outwardly from protuberance 704 so as to build up internal stresses within the membrane. During the infusion step, the internal stresses formed in membrane 700 will cause it to move toward protuberance 704 and fluid within the reservoir will be uniformly and controllably forced outwardly through a passageway 714 and then through a passageway 716 formed in base 698 in a direction toward the previously mentioned fluid flow indicator means of this latest form of the invention.

In using the apparatus of this latest form of the invention, the reservoir fill assembly is interconnected with the fluid delivery apparatus in the exact manner previously described by inserting barrel portion 660 into the receiving chamber formed in the base of the reservoir assembly and the reservoir of the fluid delivery apparatus is appropriately filled. During the reservoir filling step any air trapped within passageway 812 will be vented to atmosphere via vent element 651 and annular space 733. Similarly, any air trapped within septum mounting component 728 will be vented to atmosphere via a hydrophobic vent element 729 and a vent passageway 731 formed in connector assembly 705.

After the reservoir filling step and during the fluid dispensing step, the prestressed membrane 700 will tend to return toward a less distended configuration causing fluid within the dispenser reservoir to flow outwardly of the reservoir into passageway 714 and then into passageway 716 (FIG. 15). The fluid under pressure will next flow into passageway 740 of the inlet port of disk shaped member 742 which forms a part of the flow indicator means of the invention. The flow indicator means of this form of the invention and includes a support structure 814

Member 742 includes a downwardly extending fluid inlet leg or segment 748 (see also FIG. 5) which is provided with the previously identified fluid passageway 740. As shown in FIG. 15, passageway 740 is adapted to communicate with the reservoir of the dispenser via passageways 714 and 716 when member 742 is mated with support structure 814 in the manner indicated in FIG. 15. The dispenser flow control means of this latest form of the invention is identical to that described in connection with FIGS. 10 and 11 and function to control fluid flow outwardly of the device.

Figure 19:
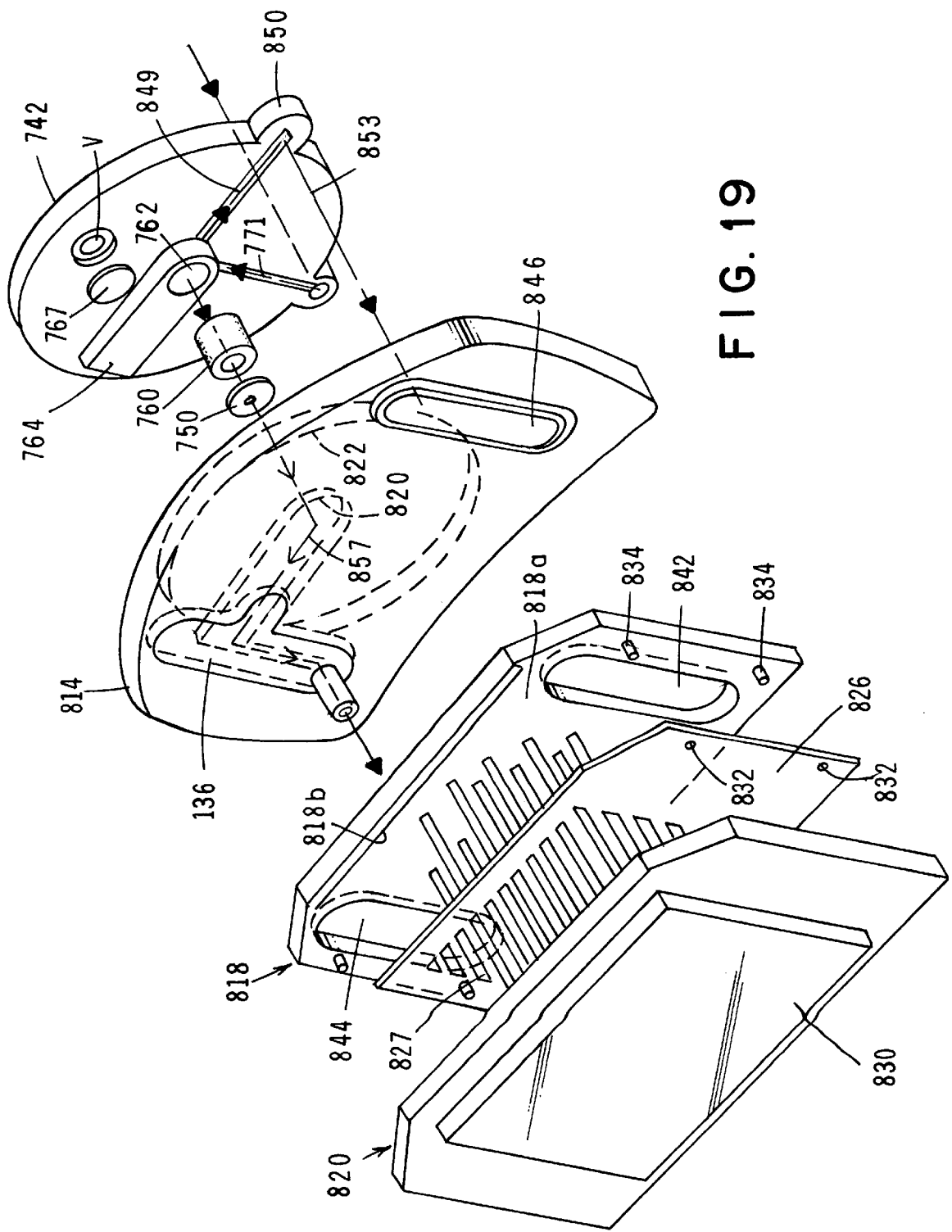
FIG. 19 is a generally perspective, exploded view of the flow indicator means of this latest form of the invention.

As before, the first flow control means includes a fluid flow rate control wafer 750, which is closely received within a cavity 820 formed in support stricture 814 (FIG. 19). Wafer 750 is held in position within cavity 820 by a tube-like, elastomeric member 760 of the character shown in FIGS. 10, 11 and 11a. When member 742 is in place within a cavity 822 of structure 814, laser drilled wafer 750 is securely positioned between the elastomeric sleeve and the bottom wall of cavity 822. As before, a vent patch 767 vents to atmosphere any air trapped within the fluid passageway of the device via a vent "V".

Turning to FIGS. 10 and 11, an alternate form of dispenser flow control means is there shown. As before, these alternate dispenser flow control means function to control fluid flow outwardly of the device. The embodiment of the invention shown in FIGS. 10 and 11 comprises a first and second flow control means. First flow control means includes a fluid flow rate control wafer 750, which is closely received within a cavity 754 found in support structure 746. Wafer 750 is held in position within cavity 754 by a tube-like, elastomeric member 760 (FIGS. 10, 11, and 11A) which is receivable within a recess 762 formed in a boss 764 provided on a disc-like member 742 (FIG. 11). Member 742 with boss 764 which is provided with a recess 762. When member 742 is in place within cavity 758 of structure 746, wafer 750 is securely positioned between elastomeric sleeve 760 and the bottom wall of cavity 754. As before, a vent patch 767 vents to atmosphere any air trapped within the fluid passageways of the device via a vent "V".

Figure 16:
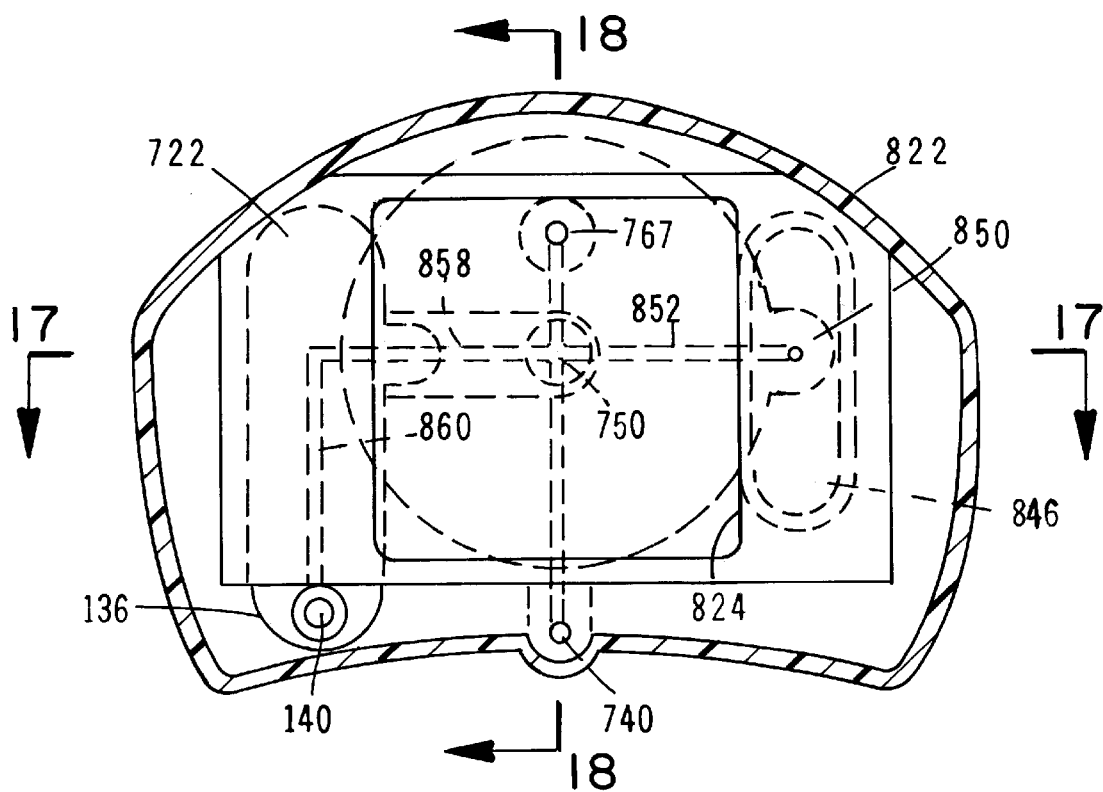
FIG. 16 is a cross-sectional view taken along lines 16—16 of FIG. 15.

With the construction described in the preceding paragraphs, when fluid is forced into passageway 714 by the stored energy means, the fluid will flow into passageway 716, then into passageway 740 of member 742 and finally in the direction of arrows 771 into chamber 762 formed in boss 764 (see FIG. 19). The fluid under pressure will then flow through the rate control frit 770 toward the fluid outlet port of the flow control subassembly. Once again, the outlet port comprises the uniquely shaped assembly 136 which is receivable in a cavity 772 formed in the back or downstream wall of support 814 (see FIGS. 11 and 16). As shown in FIGS. 11 and 16, assembly 136 includes a fluid outlet 140 and an internal chamber 142 (FIG. 10). As indicated in FIGS. 7 and 11, fluid flowing into chamber 772 will flow downwardly in the direction of the arrows 775 toward outlet 140 and into the infusion means of the apparatus.

Considering next the flow indicator means of the invention. This novel means distinguishes among two conditions of operation, namely normal fluid flow and fluid flow stop. Turning to FIG. 19, the flow indicator means here comprises an indicator base or platform 818 and a support or lens plate 820. Platform 818 and plate 820 are housed within indicator cover 822 (FIG. 18). As seen in FIGS. 18 and 20, plate 820 has a viewing lens portion 830 which indexes with an opening 824 provided in indicator cover 822.

Disposed between platform 818 and lens plate 820 is an indicia-carrying means shown here as a thin film 826. Film 826 is in intimate contact with the surface 818a of platform 818 which is printed with two integrated symbols 819 and 821 (FIGS. 20 and 21), namely a blue circle and a green arrow each consisting of diagonal strips of color printed in an alternating pattern. Film 826 serves as a "mask" over the integrated symbols and is printed with a pattern of diagonal alternating clear and opaque strips 827 that occur in a 1:2 ratio. The printed ratio of film 826 allows only one colored symbol to appear at a time when viewed through viewing lens 830 positioned on 820. Film 826 is provided at one of its ends with apertures 832 which receive retention pins 834 provided on platform 818 (FIG. 19) which permit attachment of the film to platform 818 in a manner such that pattern of clear and opaque stripes overlays the alternating patterns printed on plate 818. With this construction, film 826 is able to move in a direction parallel to the film plane with its range of motion limited to one axis in the film plane by edge guides 818b provided on platform 818. As the film moves, the visible symbol pattern changes due to the transverse displacement of the patterns 827 provided on the film.

Figure 17:
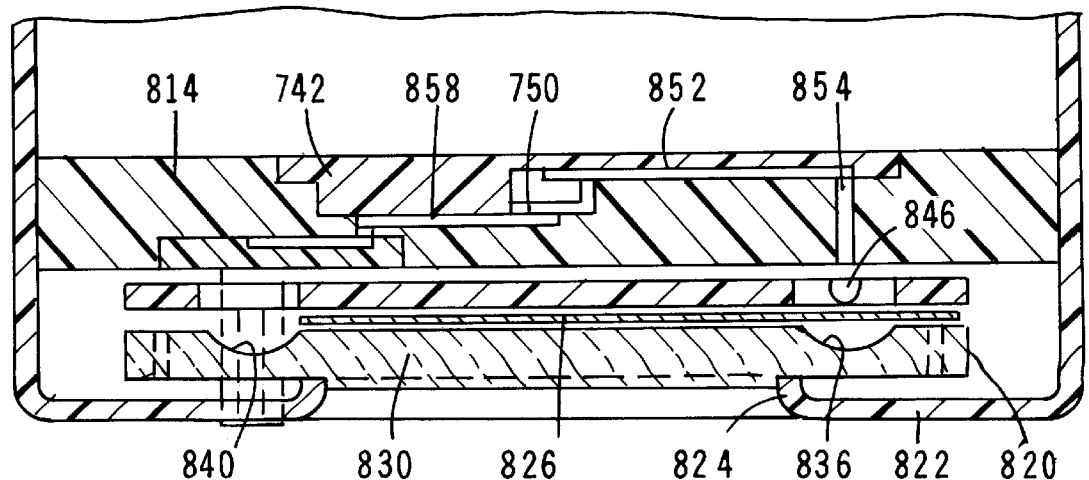
FIG. 17 is an enlarged cross-sectional view taken along lines 17—17 of FIG. 16.

As shown in FIG. 17, support plate 820 is provided with transversely spaced, channel-like depressions 838 and 840 which index with openings 842 and 844 formed in platform 818 respectively when the components are assembled in the manner shown in the drawings. Aligned with the upstream side of slot 838 is a mechanical actuator means, here provided as a mechanical actuator or elastomeric element 846.

As in the earlier described embodiments of the invention, the mechanical actuator means is deflected from its initial configuration whenever there is sufficient fluid pressure present within the fluid flow path to cause its outward deflection toward thin film 826. During operation the mechanical actuator element 846 is deflected by fluid pressure of the reservoir of the dispenser component. More particularly, when there is sufficient fluid pressure in the fluid reservoir and fluid is being delivered by the stored energy means of the device, the mechanical actuator means or elastomeric element 846 is deflected outwardly so as to urge a portion of the indicator film 826 into expansion channel 838 (FIG. 17). As the film arches into channel 838, the film is transversely displaced a specific distance. This film displacement re-aligns the front surface of the support with the mask pattern on film 826 and results in a change of the symbol (in this case an arrow as shown in FIG. 21) that is visible through the support plate view aperture 824.

A second alignment of symbol patterns as shown in FIG. 20 is visible when the device is in an unfilled state or when the delivery line is open, the reservoir is empty and fluid delivery to the patient has been completed. In this case, since there is no fluid pressure in the line to deflect the actuator, the film is not deflected and the pattern seen is the zero pattern shown in FIG. 20.

During operation of the device of this latest embodiment, when the prestressed membrane 700 tends to return toward a less distended configuration during the fluid delivery step, fluid within the reservoir will flow outwardly of reservoir, into passageway 714 and then into passageway 716 (FIG. 15). The fluid under pressure will next flow into the inlet passageway 740 formed in disc-shaped member 742. A portion of the fluid entering cavity or chamber 762 can flow in the direction of arrows 849 directly toward an ear-shaped extension 850 (FIG. 19) provided on member 742 via a flow passageway 852 (FIGS. 16 and 17). From extensions 850, the fluid will flow under pressure in the direction of the arrows 853 into pressural engagement with actuator member 846 via passageway 854 (FIGS. 16 and 17) causing it to deflect outwardly into engagement with film 826. This causes the film to deform outwardly in a manner to force a portion of indicator film to arch into expansion channel 838 (FIG. 17). This, in turn, will cause transverse displacement of indicator film 826 in the manner previously described.

As indicated in FIGS. 17 and 19, fluid flowing into chamber 762 will also flow in the direction of the arrows 857 through passageway 858 of member 814 and then into member 136. The fluid will then flow downwardly through a passageway 860 formed in member 136 (FIG. 16) and then outwardly of the device through fluid outlet 140 to which an appropriate infusion line such as line 776 can be connected.

Figure 23:
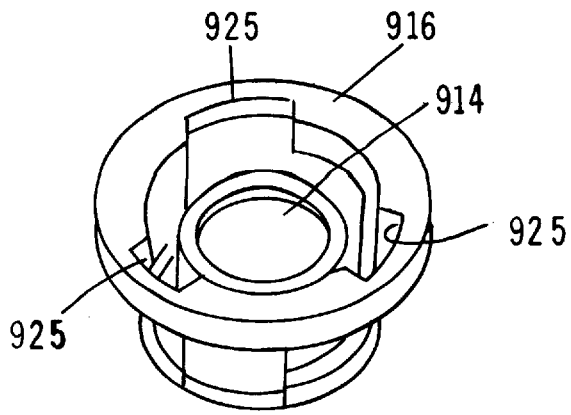
FIG. 23 is a generally perspective view of one form of the adapter component shown in FIG. 22.
Figure 23A:
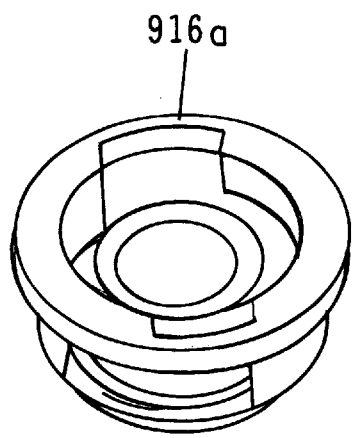
FIG. 23A is an alternate form of an adapter component.
Figure 23B:
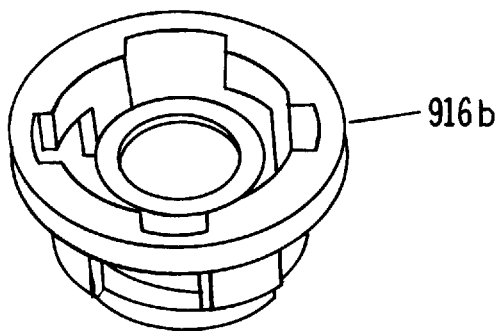
FIG. 23B is still another form of adapter component of the invention.
Figure 23C:
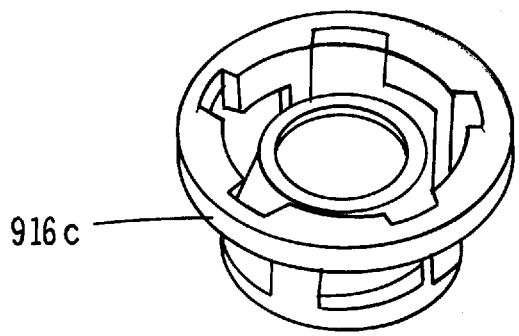
FIG. 23C is yet another form of adapter component of the invention.
Figure 23D:
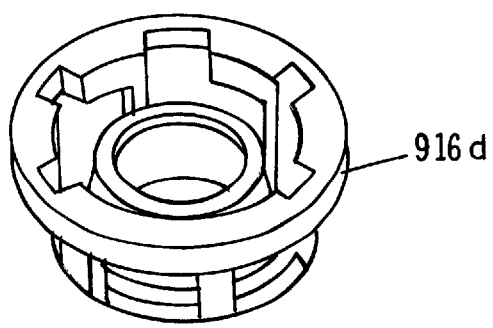
FIG. 23D is still another form of adapter component of the invention usable with the fluid dispenser component shown in FIG. 22.

Turning next to FIGS. 22 and 23, yet another form of the apparatus of the invention is there illustrated. This apparatus is similar in many respects to that shown in FIGS. 14 through 21 and like numbers are used to identify like components. Once again, the apparatus here comprises two major cooperating assemblies, namely a fluid dispensing apparatus or fluid dispenser 900 (FIGS. 22 and 23) and a reservoir fill assembly 902 (FIGS. 24 through 26D) which can be operably coupled with fluid dispenser 900. Dispenser 900 is, in turn, made up of two major cooperating subassemblies namely, a reservoir subassembly 901 (FIG. 22) and an infusion means for infusing medicinal fluids into the patient which is of the character previously described in connection with the apparatus shown in FIGS. 14 through 21.

The reservoir fill assembly 902 of the invention also comprises two major components, namely a container assembly which is identical in construction and operation to previously described container assembly 626 (FIG. 1) and an adapter assembly 904 which is quite similar in construction to adapter assembly 628 save for the provision of differently configured cap assembly.

As before, container assembly 626 is telescopically receivable within open end of the housing of the adapter assembly housing in the manner shown in FIG. 3 so that the housing can be moved from the first extended position shown in FIG. 3 to a second container encapsulation position wherein container 630 is substantially encapsulated within the housing of the adapter assembly.

As previously mentioned, the adapter assembly of this latest form of the invention includes a differently configured closure cap assembly 908 (FIGS. 24 and 25) which is connected to the body portion of the adapter assembly in the manner shown in FIG. 24. Cap assembly 908 includes a generally cylindrical exterior wall defining a barrel-like portion 910 and an outwardly tapering wall 912 which is sealably receivable within a tapered socket-like cavity 914 formed in an adapter coupler 916 provided on fluid dispenser component 900 (FIGS. 22 and 23). Adapter coupler 916 is connected by adhesive bonding or the like to a hub-like portion 920 which forms a part of a base assembly 922 and is of the configuration shown in FIG. 22.

During the dispenser reservoir filling step, fluid under pressure will flow from container 630 into the delivery device reservoir 632 which is formed between protuberance 704 and the stored energy membrane 700 (see FIG. 3). As the fluid under pressure flows into the reservoir, it will cause membrane 700 to distend outwardly from protuberance 704 so as to build up internal stresses within the membrane. During the infusion step, the internal stresses formed in membrane 700 will cause it to move toward protuberance 704 and fluid within reservoir 632 will be uniformly and controllably forced outwardly through a passageway 714 and then through a passageway 716 formed in the base in a direction toward the infusion means of the invention.

To interconnect the reservoir fill assembly 902 with the fluid delivery apparatus 900, the forward end or cap assembly portion 908 of the adapter assembly is inserted into cavity 914 of the coupler adapter 916. Formed within coupler adapter 916 are circumferentially spaced tab receiving openings or slots 925 which are adapted to receive bayonet type connector ears or tabs 927 formed on cap assembly 908 (FIGS. 22, 23, 24, and 26). Relative rotation of the fill assembly 902 and the fluid delivery apparatus 900 will securely interconnect the components in the manner previously described. As the fill assembly is mated with the delivery component, tapered wall 912 will sealably engage the wall of cavity 914 and as the adapter assembly is mated with adapter coupler 908 cannula 670 of the adapter assembly will pierce septum 726 of the fluid delivery component so that fluid can be expelled from the fluid chamber of the container assembly into the fluid reservoir of the fluid delivery apparatus 900. This step is accomplished in the manner earlier described by urging container 630 into the adapter assembly housing using the finger engaging ears. After the reservoir filling step and during the fluid dispensing step, the prestressed membrane 700 will tend to return toward a less distended configuration causing fluid within the dispenser reservoir to flow outwardly of the reservoir into passageway 714 and then into passageway 716 (FIG. 15). The fluid under pressure will next flow into passageway 740 of the inlet portion of disk shaped member 742 (see FIGS. 6, 7, 10 and 11).

Turning to FIGS. 25A, 25B, 25C, and 25D, alternate forms of the cap assembly 908 are there shown and designated by the numerals 908a, 908b, 908c and 908d respectively. Cap assembly 908a is provided with two rather than three circumferentially spaced locking tabs 927, while cap assembly 908b is provided with four rather than three circumferentially spaced locking tabs 927. Similarly, cap assembly 908c is provided with five circumferentially spaced locking tabs and cap assembly 908d is provided with six circumferentially spaced locking tabs. These alternate cap assemblies can be selectively affixed to fill assemblies which include container assemblies having containers filled with first, second, third, fourth and fifth differing medicaments.

Referring to FIGS. 23A, 23B, 23C, and 24D, there is shown alternate forms of adapter couplers 916 there designated as 916a, 916b, 916c, and 916d respectively. With the novel construction shown, fill assemblies containing a first medicament, such as morphine sulfate can be provided with a three-tab closure cap assembly 908 and the fluid delivery device can be provided with a three-slot adapter coupler 916. In like manner, fill assemblies containing a second medicament, such as a first antibiotic can be provided with a two-tab closure cap assembly 908a and the fluid delivery device can be provided with a two-slot coupler 916a. Similarly, when the fill assembly contains a third medicament such as a second antibiotic, the fill assembly can be provided with a four-tab closure cap assembly 908b, and the fluid delivery device can be provided with a four-slot coupler 916b. Similarly, fill assemblies containing other medicaments can be provided with five and six-tab closure caps which can be mated with fluid delivery devices having adapter couplers provided with five and six-slots respectively. In this way, potentially serious errors of misadministration of medicaments can be elegantly and positively avoided.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device for use in infusing medicinal fluid into a patient at a controlled rate comprising:
   (a) a fluid dispenser including:
      (i) a base having a receiving chamber having a wall;
      (ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration;
      (iii) an outlet port in communication with said outlet of said fluid reservoir for dispensing fluids from the device; and
   (b) a reservoir fill assembly interconnectable with said base of said fluid dispenser for filling said fluid reservoir thereof, said reservoir fill assembly comprising:
      (i) a container assembly including a container leaving a fluid chamber and displacement means movable within said fluid chamber;
      (ii) an adapter assembly comprising a hollow housing having an outlet in communication with said inlet of said fluid reservoir and also having a barrel portion having means for engaging said wall of said receiving chamber of said base of said fluid dispenser to connect said adapter assembly to said base, said container being telescopically receivable in said housing; and (iii) pusher means for engagement with said displacement means of said container assembly to move said displacement means within said fluid chamber to urge fluid flow toward said outlet of said adapter assembly.

2. The apparatus as defined in claim 1 in which said pusher means comprises a pusher member disposed within said hollow housing of said adapter assembly.

3. The apparatus defined in claim 1 in which said displacement means comprises a plunger member and a connector member, said connector member being interconnectable with said pusher means.

4. The apparatus as defined in claim 1 in which said chamber includes a pierceable septum and in which said adapter assembly includes a cannula for piercing said pierceable septum.

5. The apparatus as defined in claim 1 in which said displacement means comprises a plunger member and a connector member, said connector member having a pierceable wall, and in which said pusher means includes a fluid passageway and a cannula for piercing said pierceable wall.

6. The apparatus as defined in claim 1 in which said adapter assembly of said reservoir fill assembly accommodates a plurality of container assemblies.

7. A device as defined in claim 1 in which said fluid dispenser further includes fluid actuated indicator means for visually indicating fluid flow from said fluid reservoir, said indicator means comprising at least one thin film movable in response to fluid flowing from said fluid reservoir.

8. A device as defined in claim 7 in which said indicator means includes actuator means movable by fluid flowing from said reservoir between a first position wherein said actuator means is spaced from said thin film to a second position wherein said actuator means engages said thin film.

9. A device for use in infusing medicinal fluid into a patient at a controlled rate comprising:
  (a) a fluid dispenser including:
    (i) a base having, a receiving chamber having a wall;
    (ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration; and
    (iii) an outlet port in communication with said outlet of said fluid reservoir for dispensing fluids from the device;
    (iv) fluid actuated indicator means for visually indicating fluid flow from said reservoir; and
  (b) a reservoir fill assembly interconnectable with said base of said fluid dispenser for filling said fluid reservoir thereof, said reservoir fill assembly comprising:
    (i) a container subassembly including a container having a fluid chamber and displacement means movable within said fluid chamber;
    (ii) an adapter assembly comprising a hollow housing having an outlet in communication with said inlet of said fluid reservoir and also having a barrel portion having means for engaging said wall of said receiving chamber of said base of said fluid dispenser to connect said adapter assembly to said base, said container being telescopically receivable in said housing; and
    (iii) pusher means for engagement with said displacement means of said container assembly to move said displacement means within said fluid chamber to urge fluid flow toward said outlet of said adapter assembly.

10. The device as defined in claim 9 in which said fluid dispenser includes fluid recovery means for recovering fluid from said fluid reservoir.

11. The device as defined in claim 9 in which said fluid dispenser further includes vent means for venting to atmosphere gases contained within said adapter assembly.

12. The device as defined in claim 11 in which said chamber includes a pierceable septum and in which said outlet of said adapter assembly comprises a cannula for piercing said pierceable septum.

13. The apparatus as defined in claim 12 in which said vent means comprises means for venting to atmosphere gases trapped within said cannula.

14. The device as defined in claim 12 in which said displacement means comprises a plunger member and a connector member, said connector member having a pierceable wall, and in which said pusher means includes a fluid passageway and a cannula for piercing said pierceable wall.

15. The device as defined in claim 14 in which fluid actuated indicator means comprises at least one thin film, said film being movable in response to fluid flowing from said fluid reservoir.

16. A device for use in infusing medicinal fluid into a patient at a controlled rate comprising:
  (a) a fluid dispenser including:
    (i) a base having an upper surface and a lower surface, said lower surface having a dispenser connector comprising circumferentially spaced slots;
    (ii) a stored energy means for forming, in conjunction with said base, a fluid reservoir having an inlet in communication with said dispenser connector and an outlet, said stored energy means comprising at least one prestressed, distendable elastomeric membrane superimposed over said base, said membrane being further distendable as a result of pressure imparted by the fluids to be infused to establish internal stresses, said stresses tending to move said member toward a less distended configuration; and
    (iii) an outlet port in communication with said outlet of said fluid reservoir for dispensing fluids from the device; and
  (b) a reservoir fill assembly interconnectable with said fluid dispenser for filling said fluid reservoir thereof, said reservoir fill assembly comprising:
    (i) a container subassembly including a container having a body portion, a fluid chamber, and first and second ends and displacement means telescopically movable within said container from a first location proximate said second end to a second, spaced-apart location, said displacement means comprising a plunger and a connector;
    (ii) an adapter subassembly having an outlet in communication with said inlet of said reservoir, said adapter subassembly comprising a hollow housing for telescopically receiving a part of said body portion of said container of said container subassembly and a second end, said hollow housing further including an adapter connector comprising circumferentially spaced tabs mateably interconnectable with said dispenser connector of said fluid dispenser for removably interconnecting said adapter subassembly with said fluid dispenser; and
    (iii) pusher means disposed within said hollow housing for engagement with said displacement means of said container assembly to move said plunger within said container between said first and second locations to urge fluid to flow toward said outlet of said adapter subassembly, said pusher means being connected to said connector of said displacement means.

17. The device as defined in claim 16 in which said displacement means includes a pierceable wall and in which said pusher means includes a fluid passageway and a cannula for piercing said pierceable wall upon interconnection of said pusher means with said connector of said displacement means.

18. The device as defined in claim 16 further including infusion means connected to said outlet port of said fluid reservoir for infusing the medicinal fluid to the patient.

19. The device as defined in claim 18 in which said fluid dispenser further includes rate control means for controlling the rate of fluid flow toward said infusion.

20. The device as defined in claim 18 in which said fluid dispenser further includes fluid actuated indicator means disposed intermediate said fluid outlet of said reservoir, said fluid actuated indicator means comprising at least one thin film, said thin film being movable in response to fluid flow from said fluid reservoir.

21. The device as defined in claim 18 in which said adapter assembly includes fill flow control means for controlling flow from said container assembly toward said fluid reservoir of said fluid dispenser.

22. The device as defined in claim 21 in which said flow control means comprises a hollow cannula connected to said hollow housing of said adapter assembly.

23. The device as defined in claim 21 in which said flow control means comprises a valve disposed between said pusher means and said hollow cannula.

24. A device for use in infusing medicinal fluid into a patient at a controlled rate comprising:
(a) a fluid dispenser including:
  (i) a base having, a receiving chamber provided with a plurality of circumferentially spaced tab receiving openings;
  (ii) a stored energy means for forming, in conjunction with said base a fluid reservoir having an inlet in communication with said connector and an outlet, said stored energy means comprising at least one distendable member superimposed over said base, said member being distendable as a result of pressure imparted by the fluids to be infused to establish internal stresses, said stresses tending to move said member toward a less distended configuration;
  (iii) an outlet port in communication with said outlet of said fluid reservoir for dispensing fluids from the device; and
(b) a reservoir fill assembly interconnectable with said base of said fluid dispenser for filling said fluid reservoir thereof, said reservoir fill assembly comprising:
  (i) a container subassembly including a container having a fluid chamber and displacement means movable within said fluid chamber;
  (ii) an adapter assembly comprising a hollow housing having a barrel portion receivable within said receiving chamber of said base of said fluid dispenser to connect said adapter assembly to said base, said barrel portion having a plurality of circumferentially spaced tabs receivable within said tab receiving openings of said receiving chamber, said container being telescopically receivable in said housing; and
  (iii) pusher means for engagement with said displacement means of said container assembly to move said displacement means within said fluid chamber.

25. The apparatus as defined in claim 24 in which said pusher means comprises a pusher member disposed within said hollow housing of said adapter subassembly.

26. The apparatus as defined in claim 24 in which said displacement means comprises a plunger member and a connector member, said connector member being interconnectable with said pusher means.

27. The apparatus as defined in claim 24 in which said displacement means includes flow control means for controlling fluid flow through said displacement means.

28. The apparatus as defined in claim 24 further including valving means disposed within said receiving chamber of said fluid dispenser for controlling fluid flow from said reservoir fill assembly toward said fluid dispenser.

29. The device as defined in claim 24 in which said adapter assembly of said filling means further includes flow control means for controlling fluid flow from said container assembly toward said fluid dispenser reservoir.

30. The device as defined in claim 24 in which said receiving chamber of said base of said fluid dispenser includes a pair of circumferentially spaced tab receiving slots having a pair of circumferentially spaced tabs receivable within said tab receiving slots.

31. The device as defined in claim 24 in which said adapter assembly has three circumferentially spaced tabs.

32. The device as defined in claim 24 in which said adapter assembly has four circumferentially spaced tabs.

33. The device as defined in claim 24 in which said adapter assembly has five circumferentially spaced tabs.

34. The device as defined in claim 24 in which said adapter assembly has six circumferentially spaced tabs.

35. A device for use in infusing medicinal fluid into a patient at a controlled rate comprising:
(a) a fluid dispenser including:
  (i) a housing having a receiving chamber having a wall;
  (ii) a stored energy means disposed within said housing for forming a fluid reservoir having an inlet in communication with said chamber and an outlet, said stored energy means comprising at least one distendable member, said member being distendable as a result of pressure imparted by the fluids to be infused to establish internal stresses, said stressed tending to move said member toward a less distended configuration;
  (iii) an outlet port in communication with said outlet of said fluid reservoir for dispensing fluids from the device; and
(b) a reservoir fill assembly interconnectable with said housing for filling said fluid reservoir, said reservoir fill assembly comprising:
  (i) a container assembly including a container having a fluid chamber and displacement means movable within said fluid chamber;
  (ii) an adapter assembly comprising a hollow adapter housing having an outlet in communication with said inlet of said fluid reservoir and also having a barrel portion having means for engaging said wall of said receiving chamber of said housing to connect said adapter assembly to said housing; and
  (iii) pusher means for engagement with said displacement means of said container assembly to move said displacement means within said fluid chamber to urge fluid flow toward said outlet of said adapter assembly.

36. A device for use in infusing medicinal fluid into a patient at a controlled rate comprising:
(a) a fluid dispenser including (i) a housing having a receiving chamber having a wall and including a base;

(ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluid to be infused to establish internal stresses, said stresses tending to move said member toward a less distended configuration; and (iii) an outlet port in communication with said outlet of said fluid reservoir for dispensing fluids from the device;

(b) a reservoir fill assembly interconnectable with said housing for filling said fluid reservoir thereof, said reservoir fill assembly comprising:

(i) a container subassembly including a container having a fluid chamber and displacement means movable within said fluid chamber;

(ii) an adapter assembly comprising a hollow adapter housing having an outlet in communication with said inlet of said fluid reservoir and also having a barrel portion having means for engaging said wall of said receiving chamber of said housing of said fluid dispenser to connect said adapter assembly to said housing; and (iii) pusher means for engagement with said displacement means of said container assembly to move said displacement means within said fluid chamber to urge fluid flow toward said outlet of said adapter assembly.

37. The device as defined in claim 36 in which said receiving chamber includes a pierceable septum and in which said outlet of said adapter assembly comprises a cannula for piercing said pierceable septum.

38. The device as defined in claim 36 in which said displacement means comprises a plunger member and a connector member, said connector member having a pierceable wall, and in which said pusher means includes a fluid passageway and a cannula for piercing said pierceable wall.

39. The device as defined in claim 36 further including fluid actuated indicator means for visually indicating fluid flow from said reservoir, said indicator means comprising fluid flowing from said fluid reservoir.

* * * * *